(12) United States Patent
Gregory et al.

(10) Patent No.: US 10,526,614 B2
(45) Date of Patent: Jan. 7, 2020

(54) COMPOSITIONS AND METHODS FOR THE MODULATION OF ROOT HAIR PRODUCTION AND STRESS RESPONSES IN PLANTS

(71) Applicant: THE TRUSTEES OF THE UNIVERSITY OF PENNSYLVANIA, Philadelphia, PA (US)

(72) Inventors: Brian Gregory, Swedesboro, NJ (US); Shawn Foley, Ambler, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/846,699

(22) Filed: Dec. 19, 2017

(65) Prior Publication Data
US 2018/0187207 A1    Jul. 5, 2018

Related U.S. Application Data

(60) Provisional application No. 62/436,904, filed on Dec. 20, 2016.

(51) Int. Cl.
*C12N 15/82* (2006.01)
*C07K 14/415* (2006.01)

(52) U.S. Cl.
CPC ........ *C12N 15/8271* (2013.01); *C07K 14/415* (2013.01); *C12N 15/8261* (2013.01); *C12N 15/8223* (2013.01); *C12N 15/8237* (2013.01); *C12N 2840/002* (2013.01); *Y02A 40/146* (2018.01)

(58) Field of Classification Search
None
See application file for complete search history.

(56) References Cited

U.S. PATENT DOCUMENTS 8,088,975 B2 *   1/2012   Apuya ............... C12N 15/8255
                                                   435/320.1

FOREIGN PATENT DOCUMENTS

KR        2006080973    *   7/2006   ......... C12N 15/8273

OTHER PUBLICATIONS

Sjolander. Phylogenonnic inference of protein molecular function: advances and challenges. Bioinformatics. Jan. 22, 2004;20(2):170-9. (Year: 2004).*
Cruz, Jose et al., "The Dynamic Landscapes of RNA Architecture", Cell, 136: 604-609(2009).
Deal, Roger B. et al., "A Simple Method for Gene Expression and Chromatin Profiling of Individual Cell Types within a Tissue", Developmental Cell, 18: 1030-1040 (2010).
Devaiah, Ballachanda et al., "WRKY75 Transcription Factor is a Modulator of Phosphate Acquisition and Root Development in *Arabidopsis*", Plant Physiology, 143: 1789-1801 (2007).
Di Christina, Manlio et al., "The *Arabidopsis* Athb-10 (GLABRA2) is an HD-Zip protein required for regulation of root hair development", The Plant Journal, 10(3): 393-402 (1996).
Ding, Yiliang et al., "In vivo genome-wide profiling of RNA secondary structure reveals novel regulatory features", Nature, MacMillan Publishers Limited (2013).
Dolan, Liam et al., "Cellular organisation of the *Arabidopsis thaliana* root", Development, 119: 71-84 (1993).
Dong, Zhicheng et al., "The RNA-binding proteins HYL1 and SE promote accurate in vitro processing of pri-miRNA by DCL1", PNAS, 105(29): 9970-9975 (2008).
Furuta, Kaori et al., "The CKH2/PKL Chromatin Remodeling Factor Negatively Regulates Cytokinin Responses in *Arabidopsis calli*", Plant Cell Physiol., 52(4): 618-628 (2011).
Gahoonia, Tara S. et al., "A root hairless barley mutant for elucidating genetic of root hairs and phosphorus uptake", Plant and Soil, 235: 211-219 (2001).
Galway, Moira et al., The TTG Gene is Required to Specify Epidermal Cell Fate and Cell Patterning in the *Arabidopsis* Root, Developmental Biology, 166: 740-754 (1994).
Gilbert, G.A. et al., "Acid phosphatase activity in phosphorus-deficient white lupin roots", Plant, Cell and Environment, 22: 801-810 (1999).
Glisovic, Tina et al., "RNA-binding proteins and post-transcriptional gene regulation", FEBS Letters, 582: 1977-1986 (2008).
Gosai, Sager J. et al., "Global Analysis of the RNA-Protein Interaction and RNA Secondary Structure Landscapes of the *Arabidopsis* Nucleus", Molecular Cell, 57: 376-388 (2015).
Grierson, Claire et al., "Root Hairs", The *Arabidopsis* Book, American Society of Plant Biologists (2014).
Han, Hong et al., "MBNL proteins repress ES-cell-specific algterantive splicing and reprogramming", Nature, 498: 241-245 (2013).
Heckrath, G. et al., Phosphorous Leaching from Soils Containing Different Phosphorus Concentrations in the Broadbalk Experiment, J. Environ. Qual., 24: 904-910 (1995).
Jangi, Mohini et al., "Building Robust Transcriptomes with Master Splicing Factors", Cell, 159: 487-498 (2014).
Kaida, Daisuke et al., "U1 snRNP protects pre-mRNAs from premature cleavage and polyadenylation", Nature, 468: 664-668 (2010).
Kang, Na Young et al., "The AP2/EREBP GEne PUCHI Co-Acts with LBD16/ASL18 and LBD18/ASL20 Downstream of ARF7 and ARF19 to Regulate Lateral Root Development in *Arabidopsis*", Plant Cell Physiol., 54(8): 1326-1334 (2013).
Lan, Ping et al., "Mapping gene activity of *Arabidopisis* root hairs", Genome Biology, 14: R67 2(013).
Laubinger, Sascha et al., "Dual roles of the nuclear cap-binding complex and Serrate in pre-mRNA splicing and microRNA processing in *Arabidopsis thaliana*", PNAS, 105(25): 8795-8800 (2008).
Lebedeva, Svetlana et al., "Transcriptome-wide Analysis of Regulatory Interactions of the RNA-Binding Protein HuR", Molecular Cell, 43: 340-352 (2011).

(Continued)

*Primary Examiner* — Cynthia E Collins
(74) *Attorney, Agent, or Firm* — Kathleen D. Rigaut; Howson & Howson LLP

(57) ABSTRACT

Compositions and methods for modulating root hair production and stress responses in plants are provided.

5 Claims, 9 Drawing Sheets

Specification includes a Sequence Listing.

(56) References Cited

OTHER PUBLICATIONS

Meisner, C.A. et al., "Root Flair Occurrence and Variation with Environment", Argon J., 83: 814-818 (1991).
Mitsukawa, Norihiro et al., "Overexpression of an *Arabidopsis thaliana* high-affinity phosphate transporter gene in tobacco cultured cells enhances cell growth under phosphate-limited conditions", Proc. Natl. Acad. Sci. USA, 94: 1098-7102 (1997).
Muchhal, Umesh S. et al., "Phosphate transporters from the higher plant *Arabidopsis thaliana*", Proc. Natl. Acad. Sci. USA, 93: 10519-10523 (1996).
Muino, Jose M. et al., "ChIP-seq Analysis in R (CSAR): An R package for the statistical detection of protein-bound genomic regions", Plant Methods, 7: 11 (2011).
Niu, Yao Fang et al., "Responses of root architecture development to low phosphorus availability: a review", Annals of Botany, 112: 391-408 (2013).
Ogas, Joe et al., "Pickle is a CHD3 chromatin-remodeling factor that regulates the transition from embryonic to vegetative development in *Arabidopsis*", PNAS, 96:24): 13839-13844 (1999).
Patrick, W.H., "Phosphate Release and Sorption by Soils and Sediments: Effect of Aerobic and Anaerobic Conditions", Science, 186(4158): 53-55 (1974).
Peret, Benjamin et al., "Root developmental adaptation to phosphate starvation: better safe than sorry", Trends in Plant Science, 16(8): 442-450 (2011).
Poirier, Yves et al., "Phosphate Transport and Homeostasis in *Arabidopsis*", the *Arabidopsis* Book, American Society of Plant Biologists (2002).
Raczynska, Katarzyna et al., "The Serrate protein is involved in alternative splicing in *Arabidopsis thaliana* ", gucleic Acids Research, 42(2): 1224-1244 (2014).
Ray, Deepak K. et al., "Yield Trends Are Insufficient to Double Global Crop Production by 2050", PLoS One, 8(6):e66428. doi:10.1371/journal.pone.0066428 (2012).
Reymond, Matthieu et al., "Identification of QTL controlling root growth response to phosphate starvation in *Arabidopsis thaliana*", Plant, Cell and Environment, 29: 115-125 (2006).
Rosenzweig, Cynthia et al., "Potential impact of climate change on world food supply", Nature, 367: 133-138 (1994).
Ryu, Kook Hui et al., "The Werewolf MYB protein directly regulates Caprice transcription during cell fate specification in the *Arabidopsis* root epidermis", Development, 132(21) 4765-4775 (2005).
Serrano-Cartagena, J. et al., "Genetic analoysis of leaf form mutants from the *Arabidopsis* Information Service , collection", Mol. Gen. Genet., 261: 725-739 (1999).
Sharp, Phillip A., "The Centrality of RNA", Cell, 136: 577-580 (2009).
Silverman, Ian M. et al., "RNase-mediated protein footprint sequencing reveals protein-binding sites throughout the human transcriptome", Genome Biology, 15:R3 (2014).
Song, Sang-Kee et al., "Cell Fate in the *Arabidopsis* Root Epidermis is Determined by Competition between WEREWOLF and CAPRICE", Plant Physiology, 157: 1196-1208 (2011).
Streitner, Corinna et al., "An hnRNP-like RNA-binding protein affects alternative splicing by in vivo interaction with transcripts in *Arabidopsis thaliana*", Nucleic Acids Research, 40(22): 11240-11255 (2012).

Tadano, T. et al., "Secretion of acid phosphatase by the roots of crop plants under phosphorus-deficient conditions and some properties of the enzyme secreted by lupin roots", Plant and Soil, 155/156, selected papers from the Proceedings of the Twelfth International Plant Nutrition Colloquium (Oct. 1993, pp. 95-98, published by: Springer.
Tilman, David et al., "Global food demand and the sustainable intensification of agriculture", PNAS, 108(50): 20260-20264(2011).
Tominaga, Rumi et al., "Functional Analysis of the Epidermal-Specific MYB Genes Caprice and Werewolf in *Arabidopsis*", The Plant Cell, 19: 2264-2277 (2007).
Ule, Jemej et al., "CLIP Identifies Nova-Regulated RNA Networks in the Brain", Science, 302: 1212-12125 (2003).
Vandivier, Lee E. et al., "The conservation and function of RNA secondary structure in plants", Annu. Rev. Plant Biol., 67: 463-488 (2016).
Venables, Julian et al., "MBNL1 and RBFOX2 cooperate to establish a splicing programme involved in pluripotent stem cell differentiation", Nature Communications, 4:2480, doi: 10.1038/ncomms3480 (2013).
Wada, Takuji et al., "Epidermal Cell Differentiation in *Arabidopsis* Determined by a Myb Homolog, CPC", Science, 277: 1113 -1116 (1997).
Wang, Hui et al., "*Arabidopsis* WRKY45 Transcription Factor Activates Phosphate Transported ;1 Expression in Response to Phosphate Starvation", Plant Physiology, 164: 2020-2029 (2014).
Warzecha, Claude C. et al., "ESRP1 and ESRP2 Are Epithelial Cell-Type-Specific Regulators of FGFR2 Splicing", Molecular Cell, 33: 591-601 (2009).
Whittington, Angela T. et al., "MOR1 is essential for organizing cortical microtubules in plants", Nature, 411: 610-613 (2001).
Williamson, Lisa C. et al., "Phosphate Availability Regulates Root System Architecture in *Arabidopsis*", Plant Physiology, 126: 875-882 (2001).
Woo, Jongchan et al., "The response and recovery of the *Arabidopsis thaliana* transcriptome to phosphate starvation", BMC Plant Biology, 12: 62 (2012).
Yang, Li et al., "Serrate is a novel nuclear regulator in primary microRNA processing in *Arabidopsis*", The Plant Journal, 47: 841-850 (2006).
Younis, Ihab et al., "Minor introns are embedded molecular switches regulated by highly unstable U6atac snRNA", eLife, 2:e00780 (2013). doi: 10.7554/eLife.00780.
Aichinger, Ernest et al., "CHD3 Proteins and Polycomb Group Proteins Antagonistically Determine Cell Identity in *Arabidopsis*", PLoS Genet., 5(8): e1000605. doi: 10.1371/journal.pgen.1000605 (2009).
Buratti, Emanuele et al., "RNA Folding Affects the Recruitment of SR Proteins by Mouse and Human Polypurinic Enhancer Elements in the Fibronectin FDA Exon", Molecular and Cellular Biology, 24(3): 1387-1400 (2004).
Bates, T.R. et al., "Stimulation of root hair elongation in *Arabidopsis thaliana* by low phosphorus availability", Plant, well and Environment, 19: 529-538 (1996).
Berkowitz, Nathan D. et al., A comprehensive database of high-throughput sequencing-based RNA secondary structure probing data (Structure Surfer), BMC Bioinformatics, 17: 215 (2016).
Bailey, Timothy L. et al., "MEME Suite: tools for motif discovery and searching", Nucleic Acids Research, 37: W202-W208 (2009).

\* cited by examiner

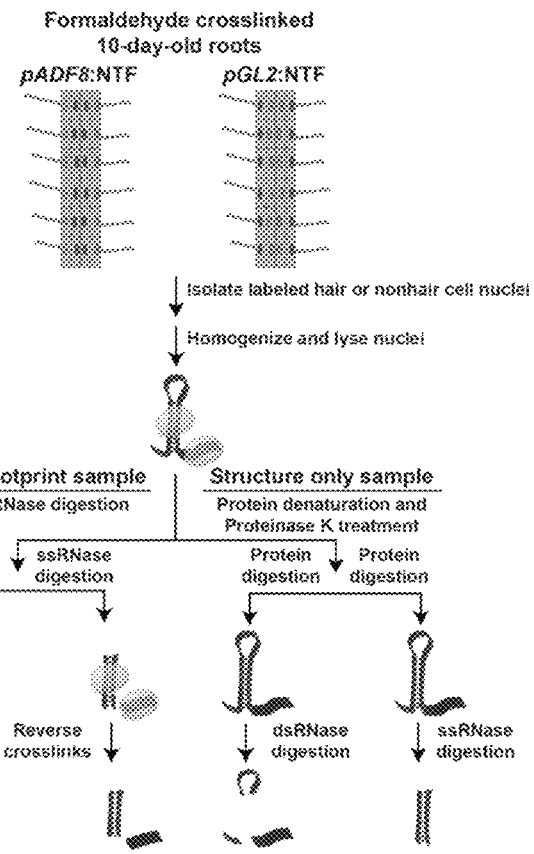
Fig. 1A
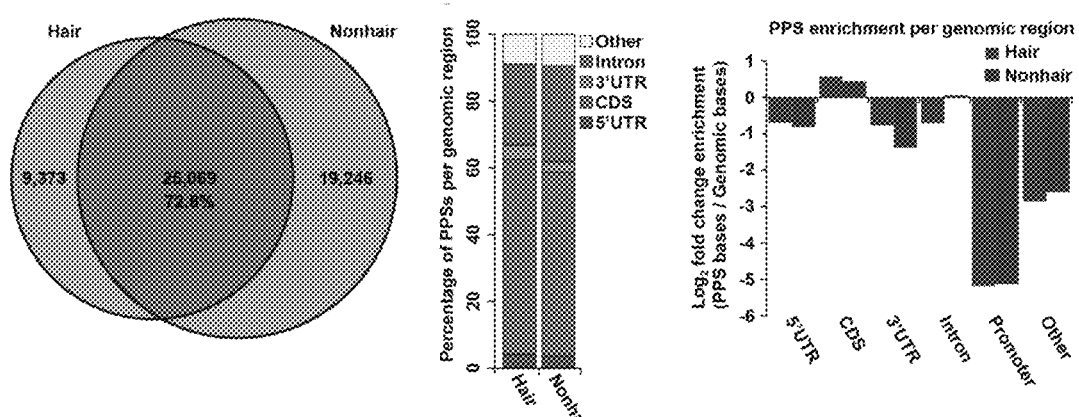
Fig. 1B
Fig. 1C
Fig. 1D

Fig. 3A
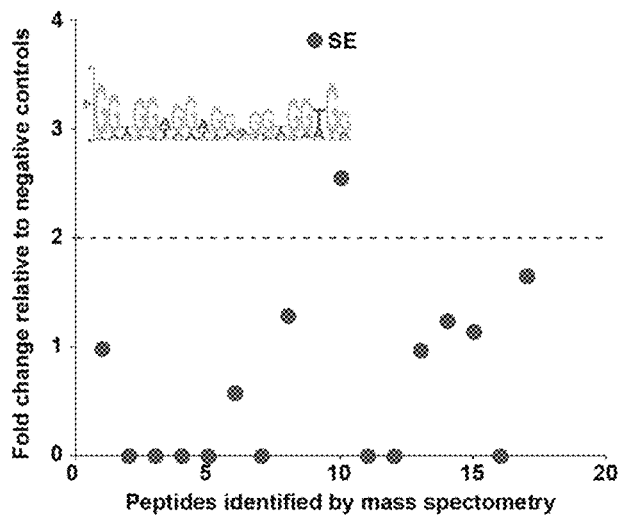
Fig. 3B
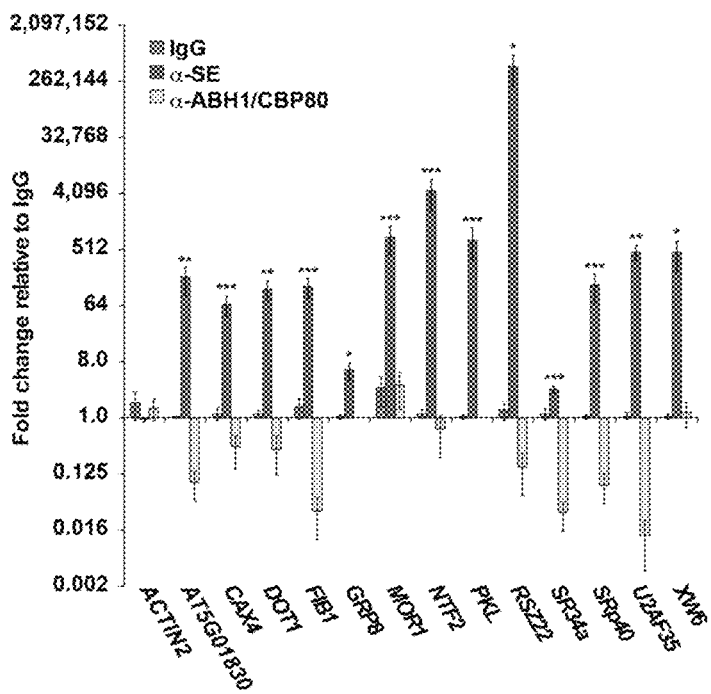
Fig. 3C
Fig. 3D

Fig. 8A

Full length CDS for GRP8 (SEQ ID NO: 1)

```
  1   ATGTCTGAAG TTGAGTACCG GTGCTTTGTC GGCGGCCTTG CCTGGGCCAC
 51   CAATGATGAA GATCTTCAAA GGACGTTCTC ACAGTTCGGC GACGTTATCG
101   ATTCTAAGAT CATTAACGAC CGCGAGAGTG AAGATCAAG GGGATTCGGA
151   TTCGTCACCT TCAAGGACGA GAAAGCCATG AGGGATGCGA TTGAAGAGAT
201   GAACGGTAAA GAGCTCGATG GACGTGTCAT CACCGTGAAC GAGGCTCAGT
251   CGAGAGGTAG CGGCGGTGGC GGAGGAGGCC GTGGTGGAAG CGGTGGTGGT
301   TACCGCAGCG GAGGCGGTGG TGGATACTCA GGAGGCGGTG GCGGCGGATA
351   CTCAGGAGGA GGCGGTGGTG GTTACGAGAG ACGTAGCGGA GGTTACGGAT
401   CTGGTGGAGG CGGTGGTGGC CGAGGATACG GTGGTGGTGG ACGCCGTGAG
451   GGAGGTGGCT ACGGAGGCGG TGATGGTGGA AGTTACGGAG GCGGTGGTGG
501   CGGCTGGTAA
```

Fig. 8B

Full length genomic sequence for GRP8: (SEQ ID NO: 2)

```
   1 AACCCTAGTT ATTACGTCAC ACCTGTTCTA TAAATTAAGG CTGCGTCTTA
  51 TCACCTCAAA TCACATAAGT CTCTCTCTTA CATTTTGAAA CCCTAATTTC
 101 TCTTCTTTTC CCCAAAAAAA AATGTCTGAA GTTGAGTACC GGTGCTTTGT
 151 CGGCGGCCTT GCCTGGGCCA CCAATGATGA AGATCTTCAA AGGACGTTCT
 201 CACAGTTCGG CGACGTTATC GATTCTAAGG TCTGTTACAC GAGAGATCGG
 251 TCTCCCGGAT CGAGCCGATT CCGATGATTC TGATCCTCGA CGGATCTGAT
 301 TCCGATCTGT TTCTCTGTTA CTTGATTCGA TTACTGTTAC TATGTTCTCT
 351 CTCGTTCTTT GTTACTGTTA CTTAATTTGT CCCATCGGTA CGTTCATCTT
 401 CCTGCTTCTA TGAGCTCGGA GATCGATCGA TTTTTGCTTT ATATTCATCG
 451 CTTTGTTTTA TATTCCTTCC ACGATTGTTT TTGCTGATGT GTATGATTTT
 501 GTTTGTTTAC AGATCATTAA CGACCGCGAG AGTGGAAGAT CAAGGGGATT
 551 CGGATTCGTC ACCTTCAAGG ACGAGAAAGC CATGAGGGAT GCGATTGAAG
 601 AGATGAACGG TAAAGAGCTC GATGGACGTG TCATCACCGT GAACGAGGCT
 651 CAGTCGAGAG GTAGCGGCGG TGGCGGAGGA GGCCGTGGTG GAAGCGGTGG
 701 TGGTTACCGC AGCGGAGGCG GTGGTGGATA CTCAGGAGGC GGTGGCGGCG
 751 GATACTCAGG AGGAGGCGGT GGTGGTTACG AGAGACGTAG CGGAGGTTAC
 801 GGATCTGGTG GAGGCGGTGG TGGCCGAGGA TACGGTGGTG GTGGACGCCG
 851 TGAGGGAGGT GGCTACGGAG GCGGTGATGG TGGAAGTTAC GGAGGCGGTG
 901 GTGGCGGCTG GTAATCAAAG ATAGAGTTGT TTGCGTGCTG CTGCTCTGTT
 951 TTTGGTTTAG ATTTGGTTTT GTGTCACCAC TTCTGGTTTG GTTATCGTTC
1001 GTTTGGTTTA CTTTTTTGAT GAAACAGTTT CGTTTAAGTC TTCTTTGTCT
1051 GGAACGAAAT GTTAATTCGC GTGTTGTTTA CTAAATTTAT AACGTTTCCT
1101 TTTAACCAGA TTCGAGATTT TCCCTCAAAT AATTTATCTT GTTAGACACA
1151 TGTATTTAAT CGAACAGCAG CTAAAGGATT C
```

Fig. 8C

Full length cDNA (SEQ ID NO: 3)

```
  1 AACCCTAGTT ATTACGTCAC ACCTGTTCTA TAAATTAAGG CTGCGTCTTA
 51 TCACCTCAAA TCACATAAGT CTCTCTCTTA CATTTTGAAA CCCTAATTTC
101 TCTTCTTTTC CCCAAAAAAA AATGTCTGAA GTTGAGTACC GGTGCTTTGT
151 CGGCGGCCTT GCCTGGGCCA CCAATGATGA AGATCTTCAA AGGACGTTCT
201 CACAGTTCGG CGACGTTATC GATTCTAAGA TCATTAACGA CCGCGAGAGT
251 GGAAGATCAA GGGGATTCGG ATTCGTCACC TTCAAGGACG AGAAAGCCAT
301 GAGGGATGCG ATTGAAGAGA TGAACGGTAA AGAGCTCGAT GGACGTGTCA
351 TCACCGTGAA CGAGGCTCAG TCGAGAGGTA GCGGCGGTGG CGGAGGAGGC
401 CGTGGTGGAA GCGGTGGTGG TTACCGCAGC GGAGGCGGTG GTGGATACTC
451 AGGAGGCGGT GGCGGCGGAT ACTCAGGAGG AGGCGGTGGT GGTTACGAGA
501 GACGTAGCGG AGGTTACGGA TCTGGTGGAG GCGGTGGTGG CCGAGGATAC
551 GGTGGTGGTG GACGCCGTGA GGGAGGTGGC TACGGAGGCG GTGATGGTGG
601 AAGTTACGGA GGCGGTGGTG GCGGCTGGTA ATCAAAGATA GAGTTGTTTG
651 CGTGCTGCTG CTCTGTTTTT GGTTTAGATT TGGTTTTGTG TCACCACTTC
701 TGGTTTGGTT ATCGTTCGTT TGGTTTACTT TTTTGATGAA ACAGTTTCGT
751 TTAAGTCTTC TTTGTCTGGA ACGAAATGTT AATTCGCGTG TTGTTTACTA
801 AATTTATAAC GTTTCCTTTT AACCAGATTC GAGATTTTCC CTCAAATAAT
851 TTATCTTGTT AGACACATGT ATTTAATCGA ACAGCAGCTA AAGGATTC
```

Fig. 8D (SEQ ID NO: 4)

Protein:

```
  1 MSEVEYRCFV GGLAWATNDE DLQRTFSQFG DVIDSKIIND RESGRSRGFG
 51 FVTFKDEKAM RDAIEEMNGK ELDGRVITVN EAQSRGSGGG GGGRGGSGGG
101 YRSGGGGGYS GGGGGGYSGG GGGGYERRSG GYGSGGGGGG RGYGGGGRRE
151 GGGYGGGDGG SYGGGGGGW
```

COMPOSITIONS AND METHODS FOR THE MODULATION OF ROOT HAIR PRODUCTION AND STRESS RESPONSES IN PLANTS

This application claims priority to U.S. Provisional Application No. 62/436,904 filed Dec. 20, 2016, the entire contents being incorporated herein by reference.

GOVERNMENT SUPPORT CLAUSE

This invention was made with government support under grant numbers MCB1243947 and IOS-1444490 awarded by the National Science Foundation. The government has certain rights in the invention.

FIELD OF THE INVENTION

This invention relates to the fields of plant metabolism and molecular biology. More specifically, the invention provides compositions and methods for modulating expression of target nucleic acids encoding proteins involved in a variety of important biochemical pathways, including those controlling root hair production and resistance to certain environmental stressors.

BACKGROUND OF THE INVENTION

Several publications and patent documents are cited throughout the specification in order to describe the state of the art to which this invention pertains. Each of these citations is incorporated herein by reference as though set forth in full.

The agricultural industry is responsible for providing food for an ever growing global population. Currently, population growth is on track to outpace agricultural growth by the year 2050 (OECD and FAO, 2012; Ray et al., 2013; Tilman et al., 2011), necessitating the development of new technologies to increase agricultural production. This challenge is compounded by climate change, which is reducing arable lands that can be used for crop production (Olesen and Bindi, 2002; Rosenzweig and Parry, 1994). Clearly, there is a need to develop plants that can better withstand drought conditions and nutrient-poor soils without compromising vegetative, fruit, or seed production. One method to achieve this is through the study of plant root development, as roots function in the uptake of both water and nutrients from the environment (Grierson et al., 2014; Hofer, 1991). Thus, these studies can result in the engineering of plants that can better tolerate and respond to these environmental stresses, without affecting the development of the agriculturally important aerial tissues.

The plant root epidermis is responsible for absorbing both water and nutrients from the environment (Grierson et al., 2014; Hofer, 1991). During root growth, epidermal precursor cells differentiate (Cormack, 1935, 1949; Dolan et al., 1993) into either root hair or non-hair cells. The long hair-like projections of hair cells dramatically increase surface area, allowing uptake of more nutrients from the surrounding soil. Therefore, plants regulate the ratio of root hair to non-hair cells in a manner that is partially dependent on environmental signals (Bates and Lynch, 1996; Ma et al., 2001; Meisner and Karnok, 1991). More specifically, plants grown under nutrient or water poor conditions develop more hair cells with longer hairs (Bates and Lynch, 1996), thereby greatly increasing the surface area of the root to promote increased absorption.

Phosphate limitation is one of the most common nutrient stresses that plants face when growing in fields for agriculture production. This is because roots can only absorb inorganic phosphates, which are naturally present at very low concentrations in soil (Heckrath et al., 1995; Patrick and Khalid, 1974).

Therefore, plants have developed numerous mechanisms by which to maximize the uptake of this nutrient in phosphate poor soil (Gahoonia et al.; Lynch and Brown; Niu et al., 2013; Williamson et al., 2001). In fact, researchers have described three major changes in *Arabidopsis thaliana* (hereafter *Arabidopsis*) root development during phosphate starvation. First, the primary root ceases downward growth, with a subsequent increase in lateral roots branching away from primary roots (Linkohr et al., 2002; Reymond et al., 2006; Williamson et al., 2001). Additionally, the root epidermis dramatically increases the number of root hair cells, while also increasing their length (Bates and Lynch, 1996). Finally, root epidermal cells secrete acid phosphatases, enzymes that catalyze organic into inorganic phosphates, which can be subsequently absorbed (Gilbert et al., 1999; Tadano et al.). Thus, there is a clear link between response to phosphate starvation and root hair cell fate. However, the molecular mechanisms by which exogenous phosphate levels regulate this cell fate decision are not fully understood.

SUMMARY OF THE INVENTION

In accordance with the present invention, a method for producing a plant exhibiting increased root hair formation and increased resistance to phosphate starvation is provided. An exemplary method comprises introducing a nucleic acid construct encoding glycine rich protein 8 (GRP8) or homologs thereof into a plant cell, thereby causing over expression of GRP8 in said plant cell, regenerating a plant from said cell, said plant exhibiting increasing root hair formation and resistance to phosphate starvation when compared to wild type plant cells lacking said nucleic acid construct. In certain embodiments, GRP8 expression is under the control of a constitutive promoter while in other embodiments, GRP 8 expression is under the control of an inducible promoter. GRP 8 expression may also be rendered tissue specific via inclusion of a tissue specific promoter in the GRP8 encoding nucleic acid construct. The invention also includes plants produced by the aforementioned method. Suitable plants for transformation include, without limitation, barley, tomato, *Brassica rapa, Camelina sativa, Zea mays*, rice, soybean and sunflower.

In yet another aspect of the invention, a plant transformation vector encoding GRP8 is provided. Plants cells comprising the aforementioned vector are also encompassed by the present invention.

BRIEF DESCRIPTION OF THE DRAWINGS

FIGS. 1A-1D: Nuclear PIP-seq identifies cell type specific RNA-protein interactions. (FIG. 1A) The PIP-seq approach in the nucleus of *Arabidopsis* root hair and non-hair cells. Fully differentiated root epidermal cells were excised from 10-day-old *Arabidopsis* plants and crosslinked with a 1% formaldehyde solution. The nuclei of either root hair or nonhair cells (green circles) were then isolated via the INTACT technique. Nuclei were lysed and separated into footprinting and structure only samples. Four total sequencing libraries were then prepared for each replicate experiment as previously described (Gosai et al., 2015). (FIG. 1B) Overlap between protein protected sites (PPSs) identified in hair (green) or nonhair (purple) cell nuclei. The intersection indicates PPSs identified in both cell types that overlap by at least a single nucleotide. (FIG. 1C) Absolute distribution of PPSs throughout regions of mRNA transcripts. (FIG. 1D) Genomic enrichment of PPS density, measured as log 2 enrichment of the fraction of PPS base coverage normalized to the fraction of genomic bases covered by indicated nuclear mRNA regions for hair (green bars) and nonhair (purple bars) cells.

(FIGS. 2A-2B) PPS density (blue line) and scaled structure score (red line) profiles for nuclear mRNAs at each nucleotide +/−100 nt from the annotated start or stop codons in hair (FIG. 2A) or nonhair (FIG. 2B) cell nuclei. The tables represent the Spearman's rho correlations between the PPS density and scaled structure scores across the graphed windows up- and downstream of the start codon, up- and downstream of the stop codon, or across all detectable mRNA transcripts. (FIG. 2C) Scaled structure score profiles at each nucleotide +/−100 nt from the annotated start or stop codons in nuclear mRNAs expressed in both hair (green line) and nonhair (purple line) cells. (FIG. 2D) PPS density profiles at each nucleotide +/−100 nt from the annotated start or stop codons in nuclear mRNAs expressed in both hair and nonhair cells. PPSs are divided into those that are detected in hair cells (green line), nonhair cells (purple line), or common to both cell types (orange line). (FIGS. 2E-2F) Scaled structure score (FIG. 2E) or PPS density (FIG. 2F) across binned unspliced lncRNAs expressed in root hair (green) or nonhair (purple) cell nuclei. Shading around the solid lines indicates standard error of the mean (SEM) across all detectable transcripts. *** indicates p value<0.001, Wilcoxon test in all panels.

FIGS. 3A-3D: SERRATE (SE) regulates hair cell fate and hair length in a partially microRNA-independent manner. (FIG. 3A) RNA affinity chromatography followed by LC-MS was performed on whole root cell lysate using the MEME identified GGN repeat motif as bait. The number of peptide spectrum matches (PSMs) for each identified peptide was graphed as fold change over the average PSMs of scrambled RNA bait and no RNA controls. Peptides above the dotted line have a more than 2-fold change and correspond to candidate RBPs. SE is denoted as being highly bound by our analysis. (FIG. 3B) RIP-qPCR was performed on whole root lysate using rabbit α-IgG (blue bars), α-SE (red bars), or α-ABH1/CBP80 (yellow bars) antibodies, graphed as fold change relative to the IgG negative control pull down, n=4. Error bars indicate standard error of mean (SEM). *, , and * denote p value<0.05, 0.01, and 0.001, respectively, Welch's t-test. (FIG. 3C-3D) Root hair length (μm) (FIG. 3C) and root hair cell density (hairs/mm) (FIG. 3D) of Col-0, se-1, abh1-8, and hyl1-5 mutant plants. For analysis of root hair length n=400, and for root hair density n>135. *, , and * denote p value<0.05, 0.01, and 0.001, respectively, while N.S. denotes p value>0.05, Wilcoxon test.

(FIGS. 4A-4C) Root hair length for null cax4-1 (FIG. 4A), mor1-1 (FIG. 4B), and pkl-1 (FIG. 4C) mutant plants as compared to wild type Col-0. For root hair length analysis n=200, and for root hair density n>70. *, , and * denote p value<0.05, 0.01, and 0.001, respectively, Wilcoxon test. (FIG. 4D) RT-qPCR of SE bound genes in WT (red) and se-1 (blue) roots, n=6. *, , and * denote p value<0.05, 0.01, and 0.001, respectively, Welch's t-test. (FIG. 4E) A model of the role of SE in both the microRNA-independent promotion of root hair termination, as well as the microRNA-dependent promotion of the nonhair cell fate is shown.

(FIG. 5A) RNA affinity chromatography followed by LC-MS was performed on whole root cell lysate using the MEME identified TG-rich motif as bait. Peptides above the dotted line have a more than 10-fold change and are candidate RBPs, with three GRPs denoted. (FIG. 5B) RIP-qPCR was performed on whole root lysate using rabbit IgG (blue bars) or rabbit serum raised against GRP7 and GRP8 (green bars) graphed as fold change relative to IgG. (FIG. 5C) Root hair cell density was measured in 8-day-old seedlings of WT or plants with decreased or increased GRP7 (grp7-1 or GRP7ox, respectively), increased GRP8 (GRP8ox), or decreased GRP7 with WT levels of GRP8 (grp7-1;8i), n>50. * and *** denote p value<0.05 and 0.001, respectively, while N.S. denotes p value>0.05, Wilcoxon test. (FIG. 5D) RT-qPCR of root tissue from lines with altered GRP7 and/or GRP8 levels, graphed as fold change relative to WT (Col-0 or Col-2). *, , and * denote p value<0.05, 0.01, and 0.001, respectively, Welch's t-test.

(FIG. 6A) RT-qPCR measuring GRP8 levels in Col-0 plants after three days of phosphate deprivation (light red bar) or control treatment (dark red bar) is shown. (FIG. 6B) Acid phosphatase activity in the roots of phosphate starved Col-0 and GRP7/8 mutant 8-day-old seedlings, n>40. (FIG. 6C) Root hair cell density (hairs/mm) in 8-day-old seedlings after three days of phosphate starvation. (FIG. 6D) Levels of phosphate starvation response genes as measured by RT-qPCR in roots from Col-0 (blue), GRP8ox (green), and grp7-1;8i (purple) grown under control conditions. For (FIG. 6A) and (FIG. 6D), * and ** denote p value<0.05 and 0.01, respectively, Welch's t-test. For (FIG. 6B) and (FIG. 6C), * and ** denote p value<0.05 and 0.01, respectively, Wilcoxon test.

(FIGS. 7D-7E) Biomass (FIG. 7D) or anthocyanin levels (FIG. 7E) for 18-day-old seedlings after 2 weeks of phosphate deprivation, n=12. For (FIG. 7A-7E), *, , and * denote p value<0.05, 0.01, and 0.001, respectively, Welch's t-test. (FIG. 7F) A model of the role of GRP8 on the plant phosphate starvation response.

FIGS. 8A-8D: GRP8 sequences. (FIG. 8A) CDS for GRP8 (SEQ ID NO: 1). (FIG. 8B) Genomic sequence encoding GRP8 (SEQ ID NO: 2). (FIG. 8C) cDNA encoding GRP8 (SEQ ID NO: 3). (FIG. 8D) Amino acid sequence of GRP8 (SEQ ID NO: 4).

DETAILED DESCRIPTION OF THE INVENTION

Figure 2A:
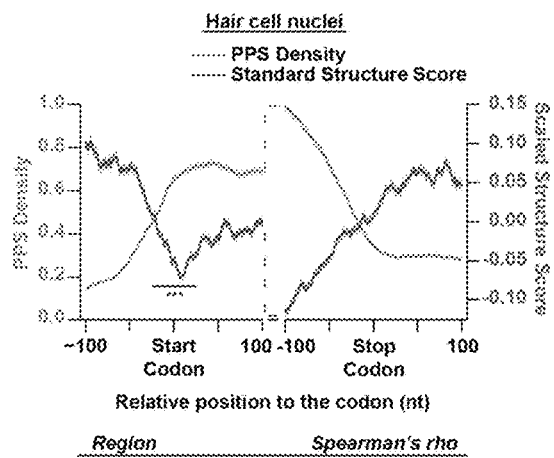
FIGS. 2A-2F: Hair and nonhair cells have distinct RNA-protein interaction and RNA secondary structure profiles.

The *Arabidopsis thaliana* root epidermis is comprised of two cell types, hair and non-hair cells, which differentiate from the same precursor. Although the transcriptional programs regulating these events are well studied, post-transcriptional factors functioning in this cell fate decision are mostly unknown. Global RNA-protein interactions and RNA secondary structure have been identified in hair and non-hair cell nuclei. This analysis reveals distinct structural and protein binding patterns across both transcriptomes, allowing identification of differential RNA binding protein (RBP) recognition sites. Using these sequences, two RBPs were identified that regulate hair cell development. Specifically, we find that SERRATE functions in a microRNA-dependent manner to inhibit hair cell fate, while also terminating growth of root hairs mostly independent of microRNA biogenesis. More significantly, we show that Glycine-rich protein 8 (GRP8) promotes hair cell fate while alleviating phosphate starvation stress.

I. Definitions

The following definitions are provided to facilitate an understanding of the present invention. Unless defined otherwise, all technical and scientific terms used herein have the same meaning as commonly understood by one of ordinary skill in the art to which this invention belongs. Generally, conventional methods of molecular biology, microbiology, recombinant DNA techniques, cell biology, and virology within the skill of the art are employed in the present invention. Such techniques are explained fully in the literature, see, e.g., Maniatis, Fritsch & Sambrook, Molecular Cloning: A Laboratory Manual (1982); DNA Cloning: A Practical Approach, Volumes I and II (D. N. Glover, ed. 1985); Oligonucleotide Synthesis (M. J. Gait, ed. 1984); Nucleic Acid Hybridization (B. D. Hames & S. J. Higgins, eds. (1984)); Animal Cell Culture (R. I. Freshney, ed. 1986); and RNA Viruses: A Practical Approach, (Alan, J. Cann, Ed., Oxford University Press, 2000).

Glycine rich protein 8 (GRP8) is a member of the glycine-rich protein (GRP) super-family which encompasses a large and complex group of plant proteins that share, as a common feature, the presence of glycine-rich domains arranged in (Gly)n-X repeats, which are involved in protein-protein interactions. GRP8 plays a role in RNA transcription or processing during stress. The protein is involved in mRNA alternative splicing of numerous targets by modulating splice site selection. GRP8 negatively regulates the circadian oscillations of its own transcript and the GRP7 transcript. Studies show that GRP8 forms an interlocked post-transcriptional negative feedback loop with the GRP7 autoregulatory circuit. Both proteins negatively autoregulate and reciprocally cross-regulate by binding to their pre-mRNAs and promoting unproductive splicing coupled to degradation via the NMD pathway.

For purposes of the invention, "nucleic acid", "nucleotide sequence" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Alternatively, this term may refer to a DNA that has been sufficiently separated from (e.g., substantially free of) other cellular components with which it would naturally be associated. "Isolated" is not meant to exclude artificial or synthetic mixtures with other compounds or materials, or the presence of impurities that do not interfere with the fundamental activity, and that may be present, for example, due to incomplete purification. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

According to the present invention, an isolated or biologically pure molecule or cell is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "promoter" or "promoter region" generally refers to the transcriptional regulatory regions of a gene. The "promoter region" may be found at the 5' or 3' side of the coding region, or within the coding region, or within introns. Typically, the "promoter region" is a nucleic acid sequence which is usually found upstream (5') to a coding sequence and which directs transcription of the nucleic acid sequence into mRNA. The "promoter region" typically provides a recognition site for RNA polymerase and the other factors necessary for proper initiation of transcription.

Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., flower vs. root). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

The term "vector" relates to a single or double stranded circular nucleic acid molecule that can be infected, transfected or transformed into cells and replicate independently or within the host cell genome. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. An "expression vector"

is a specialized vector that contains a gene or nucleic acid sequence with the necessary regulatory regions needed for expression in a host cell.

DNA constructs or vectors of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., Embo J. 3:2717-2722 (1984). Electroporation techniques are described in Fromm et al., Proc. Natl. Acad. Sci. USA 82:5824 (1985). Ballistic transformation techniques are described in Klein et al., Nature 327:70-73 (1987).

*Agrobacterium tumefaciens*-mediated transformation techniques, including disarming and use of binary vectors, are well described in the scientific literature. See, for example, Horsch et al., Science 233:496-498 (1984), and Fraley et al., Proc. Natl. Acad. Sci. USA 80:4803 (1983). Such vectors are also commercially available, e.g., GATEWAY™. Also see pGreen, which is a versatile and flexible binary Ti vector for *Agrobacterium*-mediated plant transformation.

Transformed plant cells that are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al., Ann. Rev. of Plant Phys. 38:467-486 (1987).

One of skill will recognize that after the expression cassette or vector is stably incorporated in transgenic plants and confirmed to be operable, it can be introduced into other plants by sexual crossing. Any of a number of standard breeding techniques can be used, depending upon the species to be crossed.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

As used herein, "agricultural formulations" include formulations for use in the field. The phrase "agriculturally acceptable formulation" as used herein refers to a composition or formulation that allows for the effective distribution of the nucleic acid molecules of the instant invention in the physical location most suitable for their desired activity.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxiliary agent or vehicle with which an active agent of the present invention is administered. Agriculturally acceptable carriers can be sterile liquids, such as water and oils, including those of petroleum, animal, vegetable or synthetic origin. Water or aqueous saline solutions and aqueous dextrose and glycerol solutions are preferably employed as carriers.

With respect to single-stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (see Sambrook et al. (2001) Molecular Cloning, A Laboratory Manual, Cold Spring Harbor, N.Y.: Cold Spring Harbor Laboratory Press): $Tm=81.5° C.+16.6 \text{ Log } [Na+]+0.41(\% \text{ G+C})-0.63 (\% \text{ formamide})-600/\#bp$ in duplex As an illustration of the above formula, using [Na+]=[0.368] and 50% formamide, with GC content of 42% and an average probe size of 200 bases, the Tm is 57° C. Depending upon the specific sequence involved, the Tm of a DNA duplex decreases by 0.5-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNAx at 42° C., and washed in 2×SSC and 0.5% SDS at 55° C. for 15 minutes. A high-stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

"Corresponding" means identical to or complementary to the designated sequence. The sequence may be generated in any manner, including chemical synthesis, DNA replication, reverse transcription or a combination thereof. Being "Complementary" means that a nucleic acid, such as DNA and RNA, encodes the only corresponding base pair that non-covalently connects sequences by two or three hydrogen bonds. There is only one complementary base for any of the bases found in DNA and in RNA, and skilled artisans can reconstruct a complementary strand for any single stranded nucleic acid.

The present invention also includes active portions, fragments, derivatives and functional mimetics of the GRP8 nucleic acids of the invention. A "fragment" or "portion" of a sequence means a stretch of residues of at least about five to seven contiguous residues, often at least about seven to nine contiguous residues, typically at least about nine to fifteen contiguous residues and, most preferably, at least about fourteen or more contiguous residues.

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

A "derivative" of a polypeptide, polynucleotide or fragments thereof means a sequence modified by varying the sequence of the construct, e.g. by manipulation of the nucleic acid encoding the protein or by altering the protein itself. "Derivatives" of a gene or nucleotide sequence refers to any isolated nucleic acid molecule that contains significant sequence similarity to the gene or nucleotide sequence or a part thereof. In addition, "derivatives" include such isolated nucleic acids containing modified nucleotides or mimetics of naturally-occurring nucleotides.

The term "functional" as used herein implies that the nucleic or amino acid sequence is functional for the recited assay or purpose.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide can depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein. The term "gene" refers to a nucleic acid comprising an open reading frame encoding a polypeptide, including both exon and (optionally) intron sequences. The nucleic acid may also optionally include non coding sequences such as promoter or enhancer sequences. The term "intron" refers to a DNA sequence present in a given gene that is not translated into protein and is generally found between exons.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, depending on the complexity of the target sequence, the oligonucleotide probe typically contains about 10-50 or more nucleotides, more preferably, about 15-25 nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The terms "percent similarity", "percent identity" and "percent homology" when referring to a particular sequence are used as set forth in the University of Wisconsin GCG software program.

The term "delivery" as used herein refers to the introduction of foreign molecule (i.e., GRP8 nucleic acid containing nanoparticle) into cells. The term "administration" as used herein means the introduction of a foreign molecule into a cell. The term is intended to be synonymous with the term "delivery".

The term "kit" refers to a combination of reagents and other materials.

II. Uses GRP8 Encoding Nucleic Acid Constructs

The present invention is based, at least in part, on the observation that expression of GRP8 is associated with desirable plant phenotypes such as enhanced resistance to phosphate starvation and increased root hair formation. The nucleic acids of the invention can be used to impart these phenotypes to plant species of interest. In some embodiments, the expression cassettes encoding GRP8 of the invention are prepared and introduced into plants.

Nucleic acid molecules encoding GRP8 may be prepared by using recombinant DNA technology methods. The availability of nucleotide sequence information enables preparation of nucleic acid-based molecules of the invention by a variety of means. In a preferred embodiment of the invention, a nucleic acid delivery vehicle (i.e., an expression vector) for modulating target plant phenotypes is provided wherein the expression vector comprises a nucleic acid sequence coding GRP8 or a functional fragment thereof. Administration of such expression vectors to a plant results in the modulation of root hair growth and resistance to phosphate starvation.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of GRP8. For example, the GRP8 encoding nucleic acid can be subcloned into a vector downstream of a tissue specific promoter/enhancer to target gene expression in a particular region of the plant (e.g., root, vs. leaves).

III. Agricultural Compositions

The expression vectors of the present invention may be incorporated into agricultural compositions that may be delivered to a plant. In a particular embodiment of the present invention, compositions comprising isolated nucleic acids which enable the recipient to produce biologically effective GRP8 that modulate the phenotype in the recipient plant are provided. The compositions may be administered alone or in combination with at least one other agent, such as a stabilizing compound, which may be administered in any sterile, biocompatible carrier, including, but not limited to, saline, buffered saline, dextrose, and water. In preferred embodiments, the agricultural compositions also contain a agriculturally acceptable excipient. Acceptable excipients include, but are not limited to, liquids such as water, saline, glycerol, sugars and ethanol.

After agricultural compositions have been prepared, they may be placed in an appropriate container or kit and labeled for use. For administration of GRP8 encoding vectors, such labeling would include amount, frequency, and method of delivery.

IV. Kits and Articles of Manufacture

Any of the aforementioned compositions or methods can be incorporated into a kit which may contain at least one GRP8 expression vector and means for delivering the vector to a recipient plant cell.

Hence, the present invention provides a kit comprising (a) a first component containing a GRP8 expression vector as defined hereinabove, optionally in solid form, and (b) a second component containing saline or a buffer solution (e.g. buffered saline) adapted for reconstitution (e.g. dissolution or suspension) or delivery of said vector. Preferably said saline or buffered saline has a pH in the range of 4.0-8.5, and a molarity of 20-2000 mM. In a preferred embodiment the saline or buffered saline has a pH of 6.0-8.0 and a molarity of 100-500 mM. In a most preferred embodiment the saline or buffered saline has a pH of 7.0-8.0 and a molarity of 120-250 mM.

VI. Agricultural Applications

As mentioned previously, a preferred embodiment of the invention comprises delivery of at least one GRP encoding vector to modulate root hair length and resistance to phosphate starvation. Field trials can be designed to assess the tolerability, pharmacokinetics, and pharmacodynamics of the GRP8 constructs of the invention.

The following materials and methods are provided to facilitate the practice of the present invention.

Plant Materials

Seedlings were grown on 0.5× MS plates with 1% sucrose and 0.8% Phytoblend, grown vertically at 20° C., in a 16 h light/8 h dark cycle. The purified nuclei used in this study were extracted from 10-day-old seedlings of ADF8:NTF/ACT2p:Bir A or GL2:NTF/ACT2p:BirA Columbia-0 (Col-0) ecotype of *Arabidopsis thaliana* using the INTACT methodology (Wang and Deal, 2015). Additionally, the lysates for all western blots were from these same 10-day-old seedlings.

The lysates used for RNA immunoprecipitation (RIP) RT-qPCR and motif-interacting protein analyses were from the whole roots of 8-day-old seedlings of the genotypes as noted.

Cross-Linking and INTACT Purification

Immediately before nuclei purification, 10-day-old seedlings of ADF8:NTF/ACT2p:BirA or GL2:NTF/ACT2p:BirA were crosslinked in nuclear purification buffer (20 mM MOPS (pH 7), 40 mM NaCl, 90 mM KCl, 2 mM EDTA0.5 mM EGTA) plus 1% (vol/vol) formaldehyde under vacuum for 10 minutes, followed by a five minute quench with 125 mM Glycine under vacuum for an additional five minutes. Crosslinked seedlings then underwent INTACT purification as previously described (Deal and Henikoff, 2010).

Western Blotting

Westernblots using lysates from INTACT purified nuclei or 10-day-old roots were performed using α-CNX1 (1:1,000; AS122365; Agrisera; Vännäs, Sweden), α-EIF1A (1:1,000; AS10934; Agrisera; Vännäs, Sweden), α-aldolase (1:1,000; AS08294; Agrisera; Vännäs, Sweden), or α-H3 (1:1,000; ab1791; Abcam; Cambridge, Mass., USA) antibodies were performed as previously described (Kupsch et al., 2012).

PIP-Seq Library Preparation

Approximately two million INTACT purified nuclei were lysed in 850 µl RIP buffer (25 mM Tris-HCl, pH=7.4; 150 mM KCl, 5 mM EDTA, pH=7.5; 0.5% NP40; 10 µM DTT; 1 tablet protease inhbitors and 0.5 µl/ml RNaseOUT (Life Technologies; Carlsbad, Calif., USA)) by manual grinding. The resulting cell lysate was treated with RNase-free DNase (Qiagen; Valencia, Calif., USA). The lysates were then split and treated with either 100 U/ml of a single-stranded RNase (ssRNase) (RNaseONE (Promega; Madison, Wis., USA)) with 200 µg/ml BSA in 1× RNaseONE buffer for 1 hour at room temperature (RT), or 2.5 U/ml of a double-stranded RNase (dsRNase) (RNaseV1 (Ambion; Austin, Tex., USA)) in 1×RNA structure buffer for 1 hour at 37° C. as previously described (Silverman et al., 2014). See FIG. 1A for a schematic representation of library preparation. Proteins were then denatured and digested by treatment with 1% SDS and 0.1 mg/ml Proteinase K (Roche; Basel, Switzerland) for 15 minutes at RT. Proteinase digestion was followed by a 2 hour incubation at 65° C. to reverse the RNA-protein cross-links.

To determine whether nuclease resistant regions in RNAs are due to protein binding or specific secondary structures, we also determined the digestion patterns of ds- and ssRNases immediately following protein digestion. To do this, we performed the identical treatments as described above except that the cross-linked nuclear lysates were treated with 1% SDS and 0.1 mg/ml Proteinase K (Roche; Basel, Switzerland) and ethanol precipitated prior to being treated with the two RNases. In this way, the SDS and Proteinase K solubilized and digested the proteins allowing us to deduce PPSs within all detectable RNAs in the cells of interest (see FIG. 1A for schematic).

The digested RNA was then isolated using the Qiagen miRNeasy RNA isolation kit following the included protocol (Qiagen; Valencia, Calif., USA). To ensure that only high quality RNA samples were used for PIP-seq library preparation, the purified RNA was run on a Eukaryotic Total RNA Pico Series II chip (5067-1513; Agilent Technologies; Wilmington, Del., USA) using a BioAnalyzer 2100 system. Finally, the purified RNA was used as the substrate for strand-specific sequencing library preparation as previously described (Silverman et al., 2014). All of the RNase footprinting libraries (a total of 4 for each replicate: ss- and dsRNase treatments, footprint and structure only) were sequenced on an Illumina HiSeq2000 using the standard protocol for 50 base pair single read sequencing.

Read Processing and Alignment

PIP-seq reads were first trimmed to remove 3' sequencing adapters using cutadapt (version 1.2.1 with parameters -e 0.06 -O 6 -m 14). The resulting trimmed sequences were collapsed to unique reads and aligned to the TAIR10 *Arabidopsis* genome sequence using TopHat (version 2.0.10 with parameters—library-type fr-secondstrand—read-mismatches 2—read-edit-dist 2—max-multihits 10—b2-very-sensitive—transcriptome-max-hits 10—no-coverage-search—no-novel-juncs). PCR duplicates were collapsed to single reads for all subsequent analyses.

Identification of PPSs

PPSs were identified using a modified version of the CSAR software package (Muiño et al., 2011). Specifically, read coverage values were calculated for each base position in the genome and a Poisson test was used to compute an enrichment score for footprint versus structure only libraries. PPSs were then called with a false discovery rate of 5% as previously described (Gosai et al., 2015; Silverman et al., 2014).

Calculating the Structure Score Statistic

For every base of detectable transcripts, we calculated the dsRNA-seq and ssRNA-seq coverages from the structure only samples, then calculated the structure score as described previously (Gosai et al., 2015; Li et al., 2012). Briefly, when given the dsRNA-seq and ssRNA-seq coverages ($n_{ds}$, $n_{ss}$) of a given base i, the structure score is determined as:

$$S_i = g\log(ds_i) \; g\log(ss_i) = \log_2\!\left(ds_i + \sqrt{1 + ds_i^2}\right) \log_2\!\left(ss_i + \sqrt{1 + ss_i^2}\right)$$

$$ds_i = n_{dz}\frac{\max(L_{ds}, L_{dt})}{L_{dt}}, \; ss_i = n_{xs}\frac{\max(L_{sx}, L_{xs})}{L_{xs}}$$

Where $S_i$ is the structure score, $d_{si}$ and $s_{si}$ are the normalized read converages, and $L_{ds}$, $L_{ss}$ are the total covered length by mapped dsRNA-seq and ssRNA-seq reads respectively. The total coverage length was used as the normalization constant instead of the total number of mapped reads used previously, because we believe it is a more reasonable assumption for the transcriptome to have comparable levels of paired/unpaired regions. It is of note that we used a generalized log ratio (glog) instead of normal log-odds because it can tolerate 0 values (positions with no dsRNA or ssRNA read coverage) as well as being asymptotically equivalent to the standard log ratio when the coverage values are large. Only sense-mapping reads were used, as we are entirely concerned with the intra-molecular interactions contributing to the self-folding secondary structure.

Structure Score Profile Analysis of mRNAs

The structure score for every base of each detected transcript was first calculated using all mapped and spliced reads. In addition to the minimum dsRNA-seq plus ssRNA-seq read coverage requirement discussed above, we only considered mRNAs with intact CDS regions, ≥45 nt 5'UTRs, ≥140 nt 3'UTRs and a minimum coverage of 50 reads across the entire transcript. To generate profiles, the Z score of the structure score was calculated for each nucleotide with respect to the graphed window as previously described (Berkowitz et al., 2016).

To analyze profiles across detectable lncRNAs, we divided the length of the transcript into 100 equally sized bins. Taking the average scaled structure score across each bin, we then graphed the profile of these scores.

PPS Profile Analysis of mRNAs

PPS occupancy was converted to a score at each nucleotide, with a 1 indicating that a protein was bound and a 0 indicating that the nucleotide was unbound. The average PPS occupancy was calculated for all transcripts passing the expression criteria described above. PPS density was then graphed such that the region of highest occupancy was normalized to a density of 1.0.

RNA Affinity Chromatography

We used motifs identified within PPS sequences as baits to isolate interacting proteins by affinity 'pulldown' studies. Specifically, RNA baits (covalently-linked to agarose beads) containing the identified motif of interest (IDT; Coralville, Iowa, USA) were incubated in a binding reaction (3.2 mM $MgCl_2$, 20 mM creatine phosphate, 1 mM ATP, 1.3% polyvinyl alcohol, 25 ng of yeast tRNA, 70 mM KCl, 10 mM Tris, pH 7.5, 0.1 mM EDTA) with ~56 µg of 10-day-old *Arabidopsis* whole root lysate at RT for 30 minutes. Beads were washed four times with GFB-200 (20 mM TE, 200 mM KCl) plus 6 mM MgCl$_2$ and once with 20 mM Tris-HCl (pH 7.4). The RNA-bound proteins were then directly trypsinized on the beads.

MS-Ready Sample Preparation

Multiple independent samples for the selected motifs and their corresponding controls were used to average out experimental variability, optimize detection limits, and improve signal to noise ratio for robust specific identification. MS sample preparations and analyses were performed as described previously (Onder et al., 2008; Onder et al., 2006). Briefly, RNA-bound proteins were treated directly on the beads with 100 mM NH$_4$HCO$_3$ containing ~6 ng/µl of MS-grade trypsin (Promega; Madison, Wis., USA) and incubated at 37° C. for 12-18 hrs. These samples were extracted first with 1% HCOOH/2% CH$_3$CN, and several times with 50% CH$_3$CN; combined peptide extracts were vacuum dried and desalted using a ZipTip procedure before resuspending in ~5-10 µL LC buffer A (0.1% HCOOH (v/v) in 5:95 CH$_3$CN:H$_2$O) for MS analysis.

Mass Spectrometry Analyses

Tryptic peptide extracts were analyzed using nLC-MS/MS (Dionex/LCPackings Ultimate nano-LC coupled to a Thermo LCQ Deca XP+ ion trap mass spectrometer) in duplicate. 1 µl of the peptide sample (in LC buffer A, 0.1% HCOOH (v/v) in 5:95 CH$_3$CN:H$_2$O) was first loaded onto µ-Precolumn (PepMap™ C18, LC-Packings), washed for 4 min at a flow rate of 25 µl/min with LC buffer A, then transferred onto an analytical C18-nanocapillary HPLC column (PepMapAcclaim100). Peptides were eluted at 280 nl/min flow rate with a 120 minute gradient of LC buffers A and B (0.1% (v/v) formic acid in 80:20 acetonitrile:water) ranging from 5%-95% B. A fused silica emitter tip with 8-µm aperture (FS360-75-8-N-5-C12; New Objective) mounted to a Thermo nanospray ionization (NSI) source at 1.8 kV was used for positive ionization of peptides. Mass spectra were collected using Thermo Xcalibur 2.0 software. The top 3 principal ions from each MS scan were trapped and fragmented during the chromatographic gradient, using dynamic exclusion to maximize detection of ions (range 200-2000 m/z). The trapped ions were subjected to collision-induced dissociation (CID) with He, and ~4000 spectra (MS/MS) were collected to cover the entire chromatography elution profile.

Spectral Data Analyses and Protein ID

Experimentally collected MS/MS tandem data were searched against the *Arabidopsis* Proteome Database (NCBI, latest version) using Thermo Proteome Discoverer 1.4 software. The search was restricted to full trypsin digestion with a maximum of 3 missed cleavages and potential modifications for methionine (oxidation) and cysteine (carbamidomethylation); other parameters were standard for LCQ Deca XP+ instrumentation. Peptide filters were set to standard Xcorr vs charge state values; X corr= (1.5, 2.0, 2.25, 2.5) for charges (+1, +2, +3, +4), respectively. Spectral assignments were manually scrutinized to validate the reliability of the protein identifications.

RIP-RT-qPCR

RNA immunoprecipitaion (RIP) was performed on whole root tissue from Col-0 or grp7-1 as described previously. To begin, fresh roots were submerged in PBS plus 1% (vol/vol) formaldehyde and vacuum infiltrated at room temperature (RT) for 10 minutes. One molar Glycine (Sigma-Aldrich; St. Louis, Mo., USA) was added to a final concentration of 125 mM before an additional five minutes of vacuum infiltration. The root tissue was then washed five times with distilled water, patted dry, and snap frozen in liquid nitrogen.

On the day of the RIP, the roots were ground into a fine powder in liquid nitrogen using a mortar and pestle, and resuspended in RIP buffer (150 mM NaCl, 20 mM Tris (pH=8.6), 1 mM EDTA, 5 mM MgCl$_2$, 0.5% NP40, 1 tablet/10 ml protease inhibitor (Roche; Basel, Switzerland), 0.5 µl/ml RNaseOUT (Life Technologies; Carlsbad, Calif., USA) at ~1 g/1.2 mL. This lysate was then subjected to 30 min of sonication (30 s on and 2 min off) and centrifuged twice for 15 min at max speed to remove any pelleted debris.

While the tissue is being prepared, 50 µL of Protein A beads (Life Technologies; Carlsbad, Calif., USA) were washed twice with PBS then resuspended in 400 µL. Antibodies were then added to the beads at 5-10 µg per reaction, and allowed to rotate at 4° C. for >2 hours. The antibodies used were α-SE (AS09 532, Agrisera; Vännäs, Sweden), α-ABH1/CBP80 (AS09 531, Agrisera; Vännäs, Sweden), rabbit serum raised against native recombinant *Sinapis alba* GRP10, which recognizes *Arabidopsis* GRP7 and GRP8 or normal rabbit IgG (3125, Cell Signaling Technology; Danvers, Mass., USA). The beads were then washed twice with RIP buffer, and resuspended in whole root lysate, followed by a 90 min rotation at 4° C. The RIP was then washed six times with RIP buffer, and resuspended in QIAzol. Immunoprecipitated RNA was then isolated using the miRNeasy mini kit (Qiagen; Valencia, Calif., USA), and an RT was performed on 100-200 ng of RNA using Superscript II (Ser. No. 18/064,014, Life Technologies; Carlsbad, Calif., USA) with random hexamer priming following the manufacturers protocol. The cDNA was then subjected to 15 cycles of preamplification using the SsoAdvanced PreAmp Supermix (172-5160, BioRad; Hercules, Calif., USA) kit, following the manufacturer's protocol. The preamplified template DNA was then used to perform qPCR using the 2×SYBR Green Master Mix (B21202, Bimake, Houston, Tex., USA) and following the manufacturer's protocol.

Measurement of Root Hair Density and Root Hair Length

Seeds were sterilized in a 30% Clorox solution for 15 min followed by five washes with autoclaved water. After the last wash seeds were resuspended in 0.15% sterile agarose and stratified at 4° C. for at least 48 hours. Seedlings were grown on 0.5× MS plates with 1% sucrose and 0.8% Phytoblend, grown vertically at 20° C., in a 16 h light/8 h dark cycle. Measurements of basal root hair density and length were performed on 8-day-old seedlings by imagine with a dissecting microscope and measuring root hair length using JBrowse. Root hair density was calculated by measuring a length of primary root and counting all visible hairs along that length.

For phosphate starved plants, all seeds were planted on the described 0.5× MS plates and incubated for 5 days. On the fifth day the seedling on each plate were transplanted to two new plates, one identical 0.5× MS plate and one 0.5× MS plate without phosphate. The control and starved plates were then replaced in the incubator for another three days. The root hair cell density and root hair length were then measured as described above.

For the temperature sensitive mor1-1 plants, the plants were grown at 20° C. for four days, then transferred to 31° C. for another two days before imaging and phenotyping.

Measurement of Acid Phosphatase Activity

To measure acid phosphatase activity, plants that had been phosphate starved were taken and the primary root was excised and placed in 300 µL of assay buffer (3.4 mM 4-naphthyl phosphate, 2.5 mM FastRed TR) and incubated at RT for 15 min. Then 150 µL of assay buffer was taken and absorbance at 405 nm was measured.

Measurement of Phosphate Concentration

Seedlings were germinated on 0.5× MS plates, and 5-day-old seedlings were transplanted to control or phosphate starved plates for three days. After phosphate starvation, the hypocotyl was cut to separate the seedlings into roots and shoots, and the tissue from five seedlings was pooled and weighed. This tissue was immediately placed into 1 mL of 1% glacial acetic acid and frozen in liquid nitrogen. The tissue underwent 8 rounds of freezing and thawing in liquid nitrogen and a room temperature water bath. After the eighth round of thawing, 100 µL of supernatant was taken and placed into 200 µL of water and 700 µL phosphate assay buffer (A: 2.85% $H_2SO_4$, 0.85% $NH_4MoO_4$, B: 10% ascorbic acid, A:B=6:1). The samples were then incubated at 37° C. for 60 minutes, and absorbance was measured at 810 nm (Zhang et al., 2014). A standard curve was generated and the concentration of soluble phosphate per milligram of tissue was reported.

Measurement of Anthocyanin

Seedlings were germinated on 0.5× MS plates, and 3-day-old seedlings were transplanted to control or phosphate starved plates for 14 days. After phosphate starvation, the hypocotyl was cut to separate the seedlings into roots and shoots, and the aerial tissue from five seedlings was pooled and weighed. The tissue was then submerged in a 18:1:81 solution of propanol:HCl:water, before incubation at 100° C. for 3 min. Samples were then centrifuged at >20,000× g for 15 min. The supernatant was taken and absorbance was measured at 535 nm and 650 nm. The absorbance due to anthocyanin was calculated as: $A_{anthocyanin}=A_{535}-A_{650}$.

The following Example is provided to illustrate certain embodiments of the invention. It is not intended to limit the invention in any way.

Example I

As mentioned above, there is a clear link between response to phosphate starvation and root hair cell fate. To better understand this cell fate decision, previous studies have focused primarily on understanding the transcriptional networks present in both hair and non-hair cells (Bernhardt et al., 2003; DiCristina et al., 1996; Galway et al., 1994; Lee and Schiefelbein, 2002; Masucci and Schiefelbein, 1996). Two key transcription factors that function in this process are werewolf (WER) and caprice (CPC), which promote non-hair cell (Ryu et al., 2005), and hair cell fate, respectively (Wada et al., 1997). Plants having null mutations in these genes exhibit dramatic root epidermal phenotypes. However, hair and non-hair cells are never fully absent (Kang et al., 2013; Lee and Schiefelbein, 2002; Song et al., 2011; Tominaga et al., 2007). The presence of both cell types, even when these key transcription factors are absent, suggests that there are other pathways that regulate root hair cell fate. In fact, more recent studies have begun to appreciate the numerous post-transcriptional processes that may influence this cell fate decision. Specifically, a recent study identified hair cell specific alternative splicing events (Lan et al., 2013), indicating splicing as one potential post-transcriptional mechanism of cell fate decision regulation.

Beginning with its transcription, each RNA molecule is bound by an ever-changing cohort of RNA-binding proteins (RBPs). These proteins regulate RNA stability, post-transcriptional processing (capping, splicing, etc.), export, localization, and translation (Jangi and Sharp, 2014; Kaida et al., 2010; Lewis et al., 2003; Vandivier et al., 2015; Younis et al., 2013). Furthermore, a single RBP can bind to and potentially regulate the transcripts encoded by thousands of different genes (Ule et al., 2003), allowing these proteins to act as master regulators of developmental switches (Han et al., 2013; Venables et al., 2013; Warzecha et al., 2009). However, whether RBPs regulate *Arabidopsis* root hair cell fate decisions and development is currently unknown.

Like transcription factors, RBPs bind to primary sequence motifs. However, the intricate secondary structures that each RNA forms adds an additional mechanism to regulate RBP-binding (Cruz and Westhof, 2009; Glisovic et al., 2008; Vandivier et al., 2016). More specifically, the structure of an RNA molecule can make RBP recognition sequences inaccessible to a single-stranded RNA (ssRNA) binding protein, or promote binding by a double-stranded RNA (dsRNA) binding protein, or vice versa (Buratti et al., 2001; Cooper et al., 2009; Cruz and Westhof, 2009; Sharp, 2009). Therefore, both the RNA sequence and its secondary structure are important cis regulators of RNA-protein interactions.

In the present example, we utilize our protein interaction profile sequencing (PIP-seq) technique to simultaneously probe RNA secondary structure and RNA-protein interactions in the nuclei of *Arabidopsis* root hair and non-hair cells. This analysis reveals cell type specific secondary structure and RBP binding patterns, which likely influence root epidermal cell development. Additionally, these protein-bound sequences are used to identify two RBPs, serrate and GRP8, that both regulate hair cell precursor differentiation, while SE also regulates root hair length. Further analyses reveal that GRP8 promotes phosphate uptake in the *Arabidopsis* response to phosphate starvation, thereby alleviating stress when the plant is exposed to an environment limited in this macronutrient. Together, these data elucidate the first post-transcriptional regulators of the plant root epidermal cell fate decision and development, one of which also affects a specific abiotic stress response.

Results

PIP-Seq Identifies Thousands of Cell Type Specific Protein-Bound Sites

To identify the differences in the nuclear RNA-protein interaction and RNA secondary structure landscapes of root hair and non-hair cells, we used the isolation of nuclei tagged in specific cell types (INTACT) method (Deal and Henikoff, 2010; Wang and Deal, 2015) to obtain highly pure nuclear samples. This technique utilizes cell type specific promoters to drive expression of a fusion protein that targets a biotin ligase receptor peptide to the nuclear envelope. Therefore, by using plants that expressed this fusion protein under the control of the ADF8 or GL2 promoters we were able to specifically purify nuclei from root hair and non-hair cells, respectively (FIG. 1A). In fact, we obtained highly pure nuclei from both cell types that were completely devoid of the cytoplasmic and rough endoplasmic reticulum markers EIF1A, ALDOLASE, and CNX1. These highly pure nuclei were then used for subsequent PIP-seq analyses.

PIP-seq allows global identification of RNA-protein interaction sites as well as RNA secondary structure (FIG. 1A) (Gosai et al., 2015; Silverman et al., 2014). We used ~2 million highly pure nuclei for each of two PIP-seq replicates per cell type. These nuclei were lysed, then divided into footprinting and structure only samples (four total libraries per replicate) (FIG. 1A). To globally identify RBP-bound RNA sequences, footprinting samples were directly treated with an RNase specific to either ssRNA or dsRNA (ssRNase or dsRNase, respectively), followed by protein denaturation and sequencing library preparation. In contrast, the structure only samples first had proteins denatured in SDS and degraded with Proteinase K prior to RNase digestion. Denaturation of proteins before RNase treatment makes sequences that were RBP-bound in the footprinting sample accessible to RNases in these reactions. Thus, sequences that are enriched in footprinting relative to structure only samples are identified as protein protected sites (PPSs) (Gosai et al., 2015; Silverman et al., 2014) (FIG. 1A). Additionally, using the structure only libraries allowed us to determine the native (protein-bound) RNA base-pairing probabilities for the nuclear transcriptomes of *Arabidopsis* root hair or non-hair cells, as previously described (Gosai et al., 2015; Li et al., 2012a).

The resulting PIP-seq libraries were sequenced and provided ~25-35 million raw reads per library. To determine reproducibility, we used a principle component analysis of read coverage in 500 nucleotide (nt) bins. This revealed that biological replicates of each library from the distinct cell types cluster together, indicating the high quality and reproducibility of our root hair and non-hair nuclear PIP-seq libraries.

To identify PPSs, we used a Poisson distribution model to identify enriched regions in the footprinting compared to the structure only libraries at a false discovery rate (FDR) of 5%, as previously described (Gosai et al., 2015; Silverman et al., 2014). We identified a total of 34,442 and 44,315 PPSs in root hair and non-hair cell nuclei, respectively. To estimate the functional relevance of these nuclear PPSs from both root cell types, we compared flowering plant PhastCons conservation scores (Li et al., 2012a) for PPSs and equally-sized flanking regions. We found that PPS sequences were significantly (p values<$1.2 \times 10-71$; Kolmogorov-Smirnov Test) more evolutionarily conserved than flanking regions in both hair and non-hair cells, indicating that there is evolutionary pressure to constrain these sites, likely due to their ability to interact with RBPs (Gosai et al., 2015; Silverman et al., 2014).

Additionally, we observed a high overlap of PPSs between biological replicates. Whereas CLIP-seq experiments will often find <35% of protein-bound sites shared between biological replicates (Lebedeva et al., 2011), we observed ~72% of dsRNase identified PPSs, and ~57% of ssRNase identified PPSs found in our first replicate are shared between both biological replicates, with 55-64% of hair cell and 27-36% of nonhair cell PPSs being identified by both ssRNase and dsRNase treatments. When comparing total identified PPSs found in hair cells, we observed 25,069 (72.8%) PPSs are also present in non-hair cells (FIG. 1B). Interestingly, we found 16,460 (72.4%) of dsRNase identified hair cell PPSs are common to both cell types, whereas only 4,323 (34.4%) of ssRNase identified PPSs are common, with the remaining 4,286 shared PPSs being identified in the dsRNase sample of one cell type and the ssRNase sample of the other cell type. These data reveal that many cell type specific protein-bound events are present in lowly-structured, ssRNase-accessible regions.

We next confirmed that these are true differences in protein occupancy at cell type specific PPSs, rather than a representation of differentially expressed mRNAs. To do this, we analyzed PPSs present only in mRNAs expressed in both hair and non-hair cells. We found that the PPSs from both hair and non-hair cells within this subset of transcripts displayed an overlap of 73.4%, supporting the conclusion that we have identified a subset of cell type specific RNA-protein interactions.

A classification of hair and nonhair cell PPSs revealed that >90% of these sites are localized to mRNAs, with the largest fractions occupying the coding sequence (CDS; ~55%) and introns (~25%) in both cell types (FIG. 1C). We then tested the enrichment of PPSs in specific nuclear mRNA regions (e.g., CDS, introns, etc.) by comparing the number of PPS occupied nucleotides to the number of bases annotated as each feature in the TAIR10 *Arabidopsis* genome. We found that PPSs identified in both cell types were enriched in CDSs, while underrepresented in both untranslated regions (UTRs). Furthermore, introns showed a slight enrichment for PPSs in hair cells, but an underrepresentation in nonhair cells (FIG. 1D). These findings are consistent with our previous results using nuclei isolated from whole seedlings (Gosai et al., 2015), both of which indicate that CDSs are highly RBP bound in plant nuclei.

Hair and Non-Hair Cells have Distinct RNA-Protein Interaction and RNA Secondary Structure Profiles in Shared mRNAs and lncRNAs To interrogate the landscape of RBP binding and RNA secondary structure in specific regions of nuclear mRNAs expressed in both hair and non-hair cells, we first calculated their structure scores and PPS densities. The structure score is a generalized log ratio of ds- to ssRNA-seq reads at each nucleotide position. These raw scores are then scaled by generating Z scores (Berkowitz et al., 2016), with positive and negative scores indicating high likelihood of ds- and ssRNA, respectively (see Supplemental Experimental Procedures). To examine the relationship between PPS density and structure score, we focused on the 100 nt up- and downstream of the start and stop codons of nuclear mRNAs expressed in both cell types. From this analysis, we observed the highest PPS density in the CDS with decreased occupancy within the 5' and 3' UTRs (FIGS. 2A-2B), consistent with the overall PPS localization and enrichment analysis (FIGS. 1C-1D).

In contrast to RBP occupancy, we found that secondary structure was higher in both UTRs compared to the CDS within the regions analyzed in both cell types. Additionally, we observed a significant (p values<$6.6 \times 10^{-13}$; Wilcoxon rank sum) dip in secondary structure directly over start codons, as well as upstream of the stop codon (FIGS. 2A-2B), two characteristics which have been observed in numerous studies of RNA secondary structure across various organisms (Ding et al., 2014; Gosai et al., 2015; Li et al., 2012a, 2012b). All of these results are consistent with the patterns observed previously for nuclear mRNA secondary structure from whole seedling nuclei (Gosai et al., 2015). Thus, these structural characteristics across the UTRs and CDS seem to be a consistent feature of the *Arabidopsis* nuclear mRNA transcriptome.

Consistent with our study of whole seedling nuclei, our combined analyses of RBP binding and RNA secondary structure revealed that these features are anticorrelated across nuclear mRNAs (Spearman's rho≤−0.31; p value<$2.2 \times 10^{-16}$; asymptotic t approximation) in both root epidermal cell types. In addition to this transcriptome-wide pattern for both cell types, we found even stronger anti-correlations (Spearman's rho≤−0.90; p value<$2.2 \times 10^{-16}$; asymptotic t approximation) between protein binding and RNA folding within the last 100 nt of 5' UTRs and CDSs of nuclear mRNAs expressed in both hair and nonhair mRNAs. Interestingly, we observed a discrepancy within the first 100 nt of mRNA 3' UTRs from root hair and nonhair cells. Specifically, we found a strong negative correlation (Spearman's rho≤−0.99; p value<$2.2 \times 10^{-16}$; asymptotic t approximation) between protein binding and structure in nonhair cell nuclei, with a much more mild correlation (Spearman's rho≤−0.29; p value<0.0036; asymptotic t approximation) in hair cell nuclei. This distinct pattern indicates that there may be differential protein binding in the 3' UTRs of these two cell types. Conversely, the RBP binding and RNA secondary structure of the first 100 nt of the CDS did not exhibit an anticorrelation. We found no significant correlation in hair cells, as well as a significant positive correlation (Spearman's rho>0.91; p value<$2.2 \times 10^{-16}$; asymptotic t approximation) in non-hair cells. These observations are striking as they oppose the anticorrelation that we found in this same region when profiling mixed nuclei from whole seedlings (Gosai et al., 2015). Taken together, these observations reveal a cell type specific interplay between RNA folding and RBP binding near the start codon of nuclear mRNAs.

Given that these results are from highly pure nuclear samples, the PPSs cannot simply indicate ribosome binding, and are likely caused by cell type specific RBP interactions. Identifying and characterizing these proteins will be the focus of future inquiry.

Figure 2B:
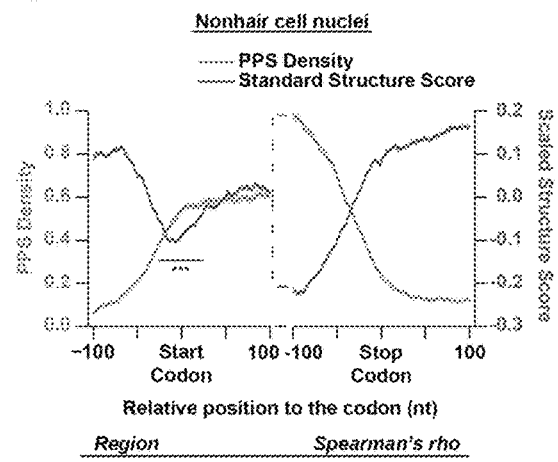
Figure 2C:
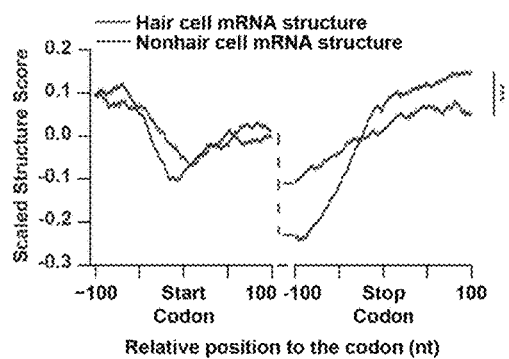
Figure 2D:
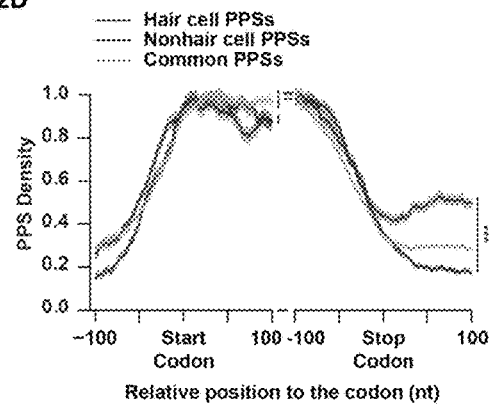

We next aimed to directly compare the RNA secondary structure patterns in the nuclei of these two cell types by comparing the average scaled structure score values (Berkowitz et al., 2016) in the 100 nt up- and downstream of the start and stop codons for the collection of mRNAs that are found in both hair and nonhair cell nuclei. We found that RNA secondary structure is similar for these mRNAs in both cell types within the 200 nt window flanking the start codon (FIG. 2C). Conversely, there are significant (p values<$3.1 \times 10^{-4}$; Wilcoxon rank sum) differences in RNA secondary structure within the 100 nt windows up- and downstream of the stop codons of the mRNAs found in both hair and nonhair cell nuclei. Specifically, we found significantly higher RNA secondary structure in these mRNAs within the last 100 nt of their CDSs in hair compared to nonhair cells, while the opposite pattern was observed for the first 100 nt of their 3' UTRs (p values<$1.7 \times 10^{-5}$ and $2.2 \times 10^{-16}$, respectively; Wilcoxon rank sum) (FIG. 2C). These differences in secondary structure around the stop codon could provide an intriguing mechanism for regulating RBP binding within these specific transcript regions. Therefore, we also directly compared the density of hair and non-hair cell specific as well as common PPSs in the 200 nt regions surrounding the start and stop codons of mRNAs expressed in both hair and non-hair cells (FIG. 2D). Although overall RBP binding had a similar profile across mRNAs from both cell types (FIGS. 2A-2B), there is a significant (p value<$3.4 \times 10^{-15}$; Wilcoxon rank sum) increase in hair cell specific RBP binding events within the first 100 nt of the 3' UTRs of mRNAs expressed in both cell types (FIG. 2D).

These findings are consistent with the significantly (p value<$2.2 \times 10^{-16}$; Wilcoxon rank sum) decreased RNA secondary structure also observed in this transcript region in hair compared to non-hair cells (FIG. 2C), given that these features are generally anti-correlated with one another (FIGS. 2A-2B). Thus, this nuclear PIP-seq analysis reveals cell type specific differences in both RNA secondary structure and RBP binding profiles between hair and non-hair cells. In total, our findings suggest that cell type specific RNA folding and RBP binding in protein-coding mRNAs is a likely mechanism for differential regulation of the root hair and nonhair cell transcriptomes, and the resulting cell fate decisions.

Figure 2E:
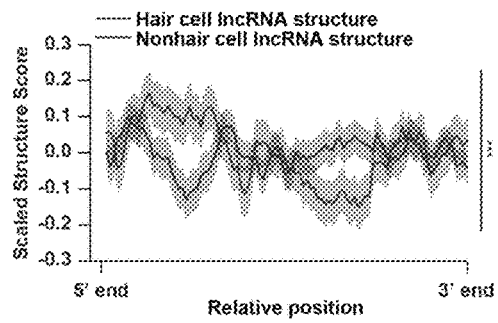

In addition to mRNAs, we examined both RNA secondary structure and RNA-protein interactions in long noncoding RNAs (lncRNAs) that are found in the nucleus. Using a comprehensive list of *Arabidopsis* lncRNAs (Liu et al., 2012), we first analyzed the secondary structure of these transcripts in root hair and nonhair cell nuclei (FIG. 2E). Taking the entire length of the unspliced annotated lncRNAs, we divided each transcript into 100 equally sized bins.

Figure 2F:
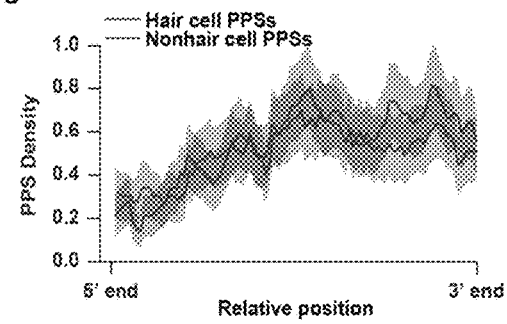

Graphing the average scaled structure score of each bin, we found significant (p value<$2.2 \times 10^{-16}$; Wilcoxon rank sum) differences between the structure profiles of the lncRNAs found in both root hair and non-hair cells. Specifically, these lncRNAs in root hair cell nuclei exhibited increased structure at the 5' end of the transcript, while being less structured near the 3' end than these lncRNAs in non-hair cell nuclei (FIG. 2E). As the structural profiles differ dramatically, we next examined PPS binding across lncRNAs. This analysis revealed that a vast majority (>82%) of lncRNA mapping PPSs in hair cells are shared with non-hair cell nuclei. Unsurprisingly, when graphing the PPS density across all lncRNAs identified in root hair or non-hair cells, these profiles were not significantly different (p value>0.05; Wilcoxon rank sum) (FIG. 2F). Therefore, like mRNAs, lncRNAs exhibit cell type specific secondary structure. However, unlike mRNAs, these differences do not result in a significant difference in RBP binding across these transcripts. Although these transcripts are bound by similar numbers of proteins in each cell type, this difference in secondary structure likely indicates that differing cohorts of proteins are binding lncRNAs in hair and non-hair cells.

SERRATE Regulates Root Hair Length and Hair Cell Fate in a microRNA-Independent and a microRNA-Dependent Manner, Respectively To determine whether cell type specific RBP binding regulates the root hair and non-hair cell fate decision, we identified RBPs that function in a cell type specific manner. To do this, we subsetted all identified PPSs into those that are hair and non-hair cell specific as well as those common to both cell types (FIG. 1B). Taking these three subsets of RBP bound sequences, we used the motif finding algorithm MEME (Bailey et al., 2009) to identify enriched protein-bound sequences. We identified a combined 54 significantly (E values<0.01) enriched motifs using these three subsets.

To identify the specific RBPs that interact with a subset of these motifs, we performed RNA affinity chromatography followed by mass spectrometry analysis. In this technique, we covalently attached a synthetic RNA motif or a scrambled sequence control to agarose beads. We then incubated these RNA baits, as well as a bead-only control, with whole root lysate, and stringently washed away any weakly bound proteins. The specifically bound proteins were identified via mass spectrometry. Using this approach, we identified 58 annotated RBPs that are at least 4-fold enriched for interaction with at least one of the twelve tested sequence motifs, as compared to the scrambled sequence and bead-only negative controls. One motif of particular interest, a GGN repeat motif that was enriched in PPSs common to both root hair and non-hair cell nuclei, was found to interact with the RBP SERRATE (SE) (AT2G27100) (FIG. 3A). SE is known to function in conjunction with ABA HYPERSENSITIVE 1/CAP-BINDING PROTEIN 80 (ABH1/CPB80, AT2G13540) and HYPONASTIC LEAVES 1 (HYL1, AT1G09700) in microRNA (miRNA) biogenesis, where these three RBPs recruit DICER-LIKE 1 (DCL1, AT1G01040) to primary miRNA transcripts to allow their processing to mature miRNAs (Dong et al., 2008; Lobbes et al., 2006; Yang et al., 2006). Additionally, SE and ABH1/CBP80 regulate alternative splicing across the *Arabidopsis* transcriptome. This variety of functions indicated that SE was a reasonable candidate as a potential regulator of root hair cell fate. To confirm that SE interacts with transcripts containing the GGN repeat motif in vivo, we performed RNA immunoprecipitation (RIP) followed by RT-qPCR. To do this, we incubated lysates from formaldehyde crosslinked roots with polyclonal α-SE, α-ABH1/CBP80, or the negative control rabbit IgG antibody. We first confirmed pulldown of SE and ABH1/CBP80 by these antibodies, then performed RT-qPCR for 13 GGN repeat containing mRNAs. We found that all 13 of the transcripts were significantly (all p values<0.05; Welch's t-test) enriched >1.5-fold in the α-SE compared to the IgG control RIP samples, as opposed to the ACTIN2 negative control (FIG. 3B). Furthermore, none of the 13 transcripts were enriched in α-ABH1/CBP80 compared to the IgG control RIP samples. Taken together, these findings indicate that SE interacts in vivo with GGN motif-containing mRNAs, while ABH1/CBP80 does not.

After validating in vivo GGN motif-containing mRNA binding by SE, we next determined whether this protein regulates root hair cell fate and development. To do this, we measured the root hair cell density (hairs/mm) and root hair length in 8-day-old wild type Col-0 (hereafter WT) and SE hypomorphic (se-1) seedlings (Clarke et al., 1999; Serrano-Cartagena et al., 1999). From this analysis, we found that se-1 mutant seedlings had significantly (p values<$2.2\times10^{-16}$; Wilcoxon test) more root hair cells that are significantly (p values<$2.2\times10^{-16}$; Wilcoxon test) longer as compared to WT (FIGS. 3C-3D), indicating that SE functions in both promoting root non-hair cell fate and terminating root hair extension. The difference in hair cell density on se-1 plants could be caused by either increased hair cell fate decisions, resulting in ectopic hair cells, or by decreased epidermal cell size, packing hair cells closer together. Therefore, we measured the size of hair cell bodies and found that there is no significant (p value>0.05; Wilcoxon test) difference in their size in se-1 compared to WT roots. Combined, these findings demonstrate that SE functions both in precursor epidermal cells to promote non-hair cell fate, as well as in differentiated hair cells to terminate hair growth. This variety of functions is unsurprising as this RBP binds (FIG. 3B) and post-transcriptionally regulates many different transcripts (Clarke et al., 1999; Laubinger et al., 2008; Lobbes et al., 2006; Raczynska et al., 2014; Yang et al., 2006).

As SE functions in both microRNA biogenesis and alternative splicing, our next goal was to differentiate the effect of these two regulatory mechanisms on its function in root hair cell development. To do this, we looked for root hair length and density phenotypes in null mutants of ABH1/CBP80 (abh1-8) and hypomorphic mutants of HYL1 (hyl1-5), both of which are known to function in conjunction with SE during plant miRNA biogenesis. We measured root hair density for 8-day-old WT, abh1-8, and hyl1-5 seedlings and found significant (p values<$5.6\times10^{-15}$; Wilcoxon test) increases in the density of root hairs in both abh1-8 and hyl1-5 mutant compared to WT (FIG. 3C). These increases were similar in magnitude to those seen in the se-1 mutant seedlings, indicating that this root hair cell fate phenotype is miRNA biogenesis dependent. Additionally, we found the root hair lengths in abh-1 and hyl1-5 seedlings to be significantly (p values<$3.7\times10^{-9}$; Wilcoxon test) longer than those of WT. However, they are also significantly (p values<$2.2\times10^{-16}$; Wilcoxon test) shorter than those observed for se-1 seedlings (FIG. 3D). This mild increase in hair length in abh1-8 and hyl1-5 mutant roots indicates that decreased miRNA biogenesis in se-1 plants accounts for a portion of the root hair length phenotype. However, there are also important SE-specific regulatory functions that add to the increased hair length observed in se-1 mutant seedlings. Taken together, these findings reveal that although the function of SE in the microRNA biogenesis pathway is required for regulating root hair cell fate, this protein also has specific effects on root hair length.

In order to better understand these SE-specific effects on hair length, we investigated the root phenotypes of mutants lacking one of several GGN motif-containing genes that we found were bound by SE (FIG. 3B). Although none of these genes are known to function in root hair cell fate, three of them have known roles in root development. CATION EXCHANGER 4 (CAX4, AT5G01490) is a H+/$Ca^{2+}$ cation exchange pump, which promotes both primary and lateral root growth in plants subjected to $Cd^{2+}$ toxicity (Mei et al., 2009). MICROTUBULE ORGANIZATION 1 (MOR1, AT2G35630) regulates microtubule assembly, and when temperature sensitive mor1-1 mutants are grown at the restrictive temperature there is an increase in primary root diameter (Whittington et al., 2001). Additionally, the chromatin-remodeling factor PICKLE (PKL, AT2G25170) is necessary for silencing embryonic genes and promoting lateral root development (Aichinger et al., 2009; Furuta et al., 2011; Ogas et al., 1999).

Figure 4A:
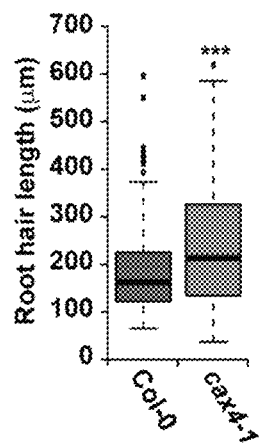
FIGS. 4A-4E: SE bound GGN motif containing genes regulate root hair cell development.
Figure 4B:
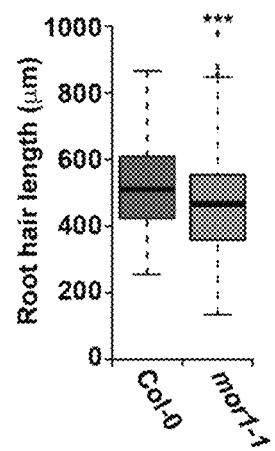
Figure 4C:
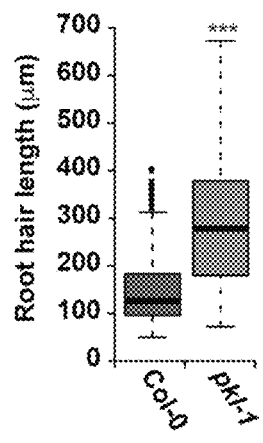
Figure 4D:
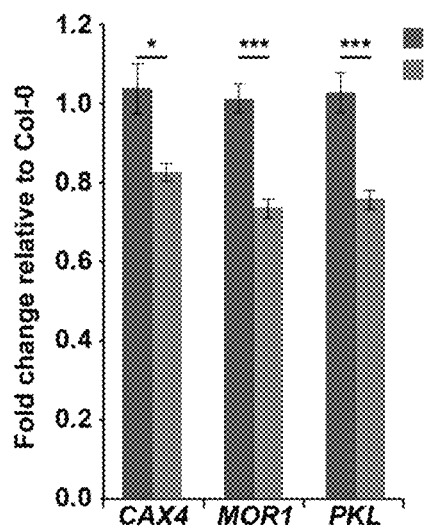
Figure 4E:
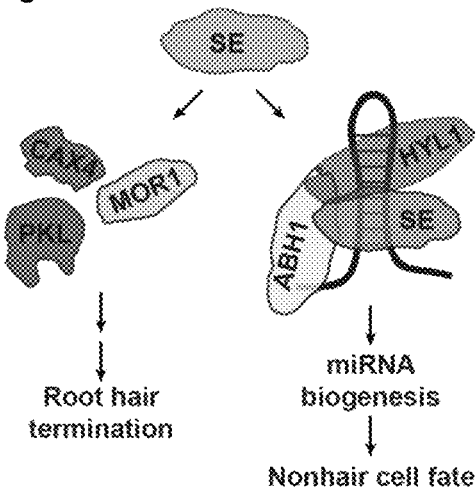

Interestingly, when screening 8-day-old seedlings lacking any one of these proteins (cax4-1, mor1-1, and pkl-1) we found significantly (all p values<0.001; Wilcoxon test) aberrant root hair length as compared to WT (FIGS. 4A-4C). Specifically, we observed that cax4-1 and pkl-1 mutant seedlings had longer root hairs (FIGS. 4A and 4C), similar to se-1. Conversely, we found that mor1-1 mutant seedlings grown at the restrictive temperature displayed shorter root hairs compared to WT (FIG. 4B). Taken together, these data suggest that the increased root hair length observed for se-1 plants is likely due to the additive effects of misregulation of numerous mRNA substrates. To test this hypothesis, we measured expression of these three genes in the roots of WT and se-1 plants. We found that all three genes are significantly (all p values<0.05; Welch's t-test) decreased in se-1 roots (FIG. 4D). In total, our results suggest that SE promotes the nonhair cell fate in a miRNA biogenesis dependent manner, while also terminating root hair growth by stabilizing the mRNA transcripts of proteins involved in specifying hair length in plant roots (FIG. 4E).

GRP8 Regulates Root Hair Cell Fate Independently of GRP7

Figure 5A:
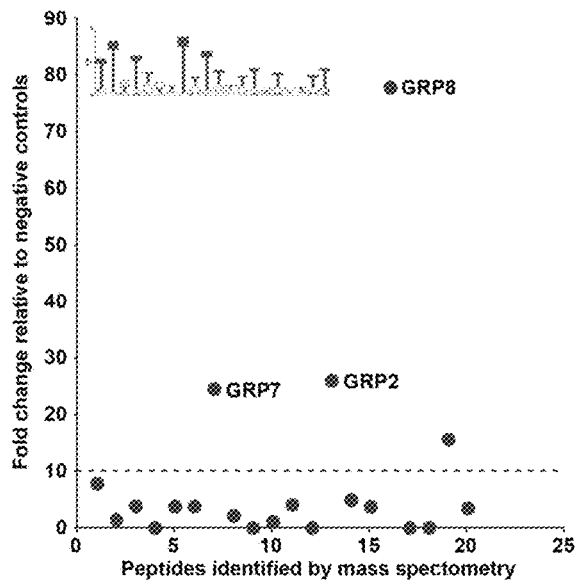
FIGS. 5A-5D: GRP8 regulates root hair cell fate in a GRP7-independent manner.
Figure 5B:
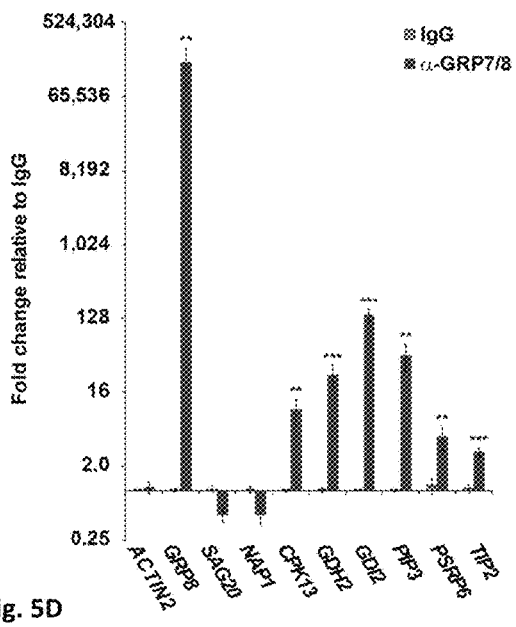

Another RBP bound motif of interest is the TG-rich motif identified within the hair cell specific set of PPSs. We performed RNA affinity chromatography and found four annotated RBPs were >10-fold enriched over our negative controls. In addition to RBP45A (AT4G54900), we found multiple members of the family of GLYCINE-RICH PROTEINs, GRP2 (AT14G13850), GRP7 (AT2G21660), and GRP8 (AT4G39260) interacted with this sequence motif (FIG. 5A). GRPs are nuclear localized hnRNP-like proteins (Streitner et al., 2012) that are required for numerous processes in plants, including responses to various biotic and abiotic stresses via their function in regulating both alternative splicing and microRNA biogenesis (Lewinski et al., 2016). Using an antibody that recognizes both native GRP7 and GRP8, we performed RIP-qPCR to validate in vivo binding of GRP7/8 to TG-rich motif containing transcripts in formaldehyde-crosslinked whole root lysate. Given that both GRP7 and GRP8 are known to bind the GRP8 transcript (Schöning et al., 2008), we used it as a positive control, and identified a significant enrichment of this transcript in the α-GRP7/8 compared to our rabbit IgG negative control pulldown (FIG. 5B). Of the eight TG-rich motif containing mRNAs tested, we found six genes to be significantly (all p values<0.05; Welch's t-test) enriched in the α-GRP7/8 compared to the IgG negative control pulldown (FIG. 5B). These data reveal either GRP7, GRP8, or both proteins bind to TG-rich motif-containing transcripts in vivo.

As the GRP7/8 bound motif was enriched specifically in hair cell PPSs, we tested plants aberrantly expressing these proteins for root hair cell phenotypes.

Figure 5C:
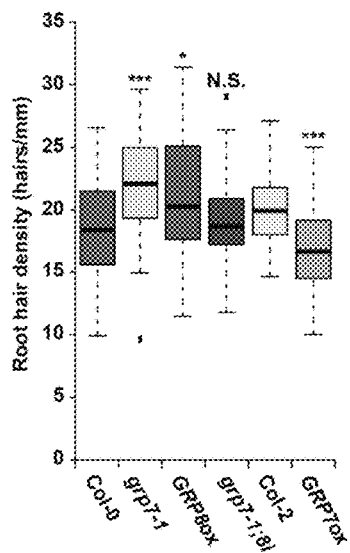
Figure 5D:
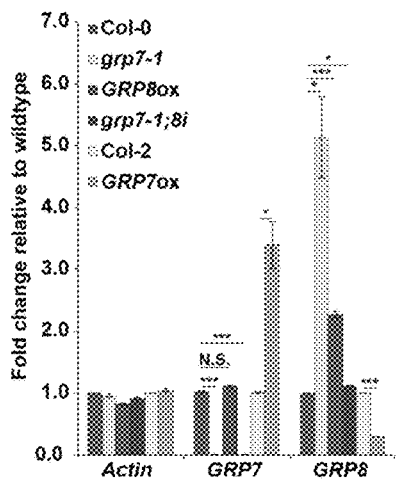

From this analysis, we found that root hair cell density in the grp7-1 null mutant is significantly (p value<$3.3\times10^{-7}$; Wilcoxon test) increased compared to WT plants (FIG. 5C). In accordance, plants overexpressing GRP7 (GRP7ox) demonstrate significantly (p value<$2.8\times10^{-8}$; Wilcoxon test) decreased hair cell density compared to their respective WT plants (Col-2) (FIG. 5C). As mentioned previously, GRP7 is known to bind to GRP8 transcripts, thereby decreasing GRP8 expression levels (Schöning et al., 2008), resulting in the grp7-1 and GRP7ox lines exhibiting significantly (p values<0.05; Welch's t-test) increased or decreased GRP8 levels as compared to WT plants, respectively (FIG. 5D). Thus, to differentiate the effects of each protein in hair cell differentiation, we required additional mutant plant lines. For instance, we identified a mutant line with an insertion in the GRP8 promoter (SAIL_75_G05; hereafter referred to as GRP8ox) that resulted in a significant (p value<0.001; Welch's t-test) increase in the levels of GRP8 mRNA in these plants relative to WT. Importantly, this increase in GRP8 levels does not cause a concomitant alteration in GRP7 abundance in GRP8ox plants (FIG. 5D). We examined root hair cell density in these plants, and revealed a significantly (p value<0.015; Wilcoxon test) increased root hair density as compared to WT, strongly suggesting that this is a GRP8-dependent phenotype (FIG. 5C). To determine the effects of altering GRP7 alone on root hair cell fate, we also measured the density of these cells in a plant line that contains a GRP7 null mutation (grp7-1), as well as an artificial microRNA targeting GRP8, which returns the levels of this mRNA close to those of WT (hereafter grp7-1;8i) (Streitner et al., 2012) (FIG. 5D). We found that these plants exhibit a similar root hair density as WT (p value>0.825; Wilcoxon test) (FIG. 5C), indicating that this is indeed a GRP7 independent phenotype. Therefore, the grp7-1 plants only exhibited increased root hair cell density as a result of increased GRP8 levels, not due to the absence of GRP7. Lastly, we confirmed that this phenotype was due to ectopic hair cell production, rather than changes in the size of epidermal hair cells. Combined, these data reveal that GRP8 promotes root hair cell fate in a GRP7 independent manner, uncovering another novel post-transcriptional regulator of this important plant developmental process.

GRP8 Promotes Phosphate Starvation Stress Response

Figure 6A:
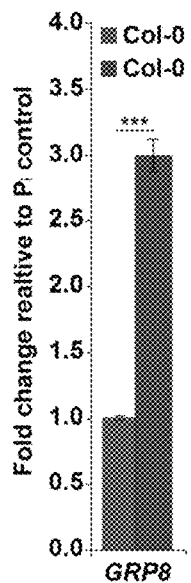
FIGS. 6A-6D: GRP8 functions in the phosphate starvation response pathway.
Figure 6B:
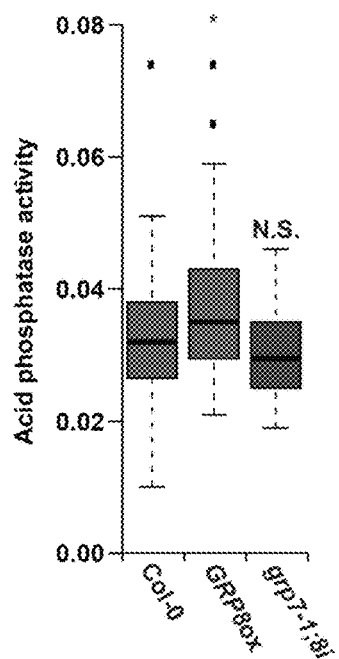

One of the major factors regulating root hair cell fate is environmental signaling, such as nutrient deprivation. Therefore, a regulator of root hair cell fate may play a role in nutrient stress response. In fact, a recent microarray analysis of phosphate starved *Arabidopsis* roots revealed a mild increase in GRP8 levels during the phosphate starvation response (Woo et al., 2012). Given this observation, in conjunction with our identification of GRP8 as a regulator of root hair cell fate (FIGS. 5A-5D), we next investigated the role of this RBP in the phosphate starvation stress response pathway. To begin, we performed RT-qPCR on the roots of WT plants grown on control and low phosphate media and validated that GRP8 expression is significantly (p value<$1.1\times10^{-9}$; Welch's t-test) upregulated upon phosphate starvation (FIG. 6A), thereby verifying that this gene does respond to phosphate deprivation. We then examined the response of WT, GRP8ox, and grp7-1;8i plants to phosphate starvation. Using these plants, we first measured the levels of acid phosphatase activity from their roots under control and 3-day phosphate starvation conditions. This analysis reveals acid phosphatase levels to be significantly (p value<0.05; Wilcoxon test) increased in the GRP8ox plants as compared to WT (FIG. 6B) with no significant (p value>0.05; Wilcoxon test) difference between grp7-1;8i and WT plants (FIG. 6B).

These results indicate that there is a GRP8-dependent and GRP7-independent increase in acid phosphatase activity in *Arabidopsis* roots upon phosphate starvation.

Figure 6C:
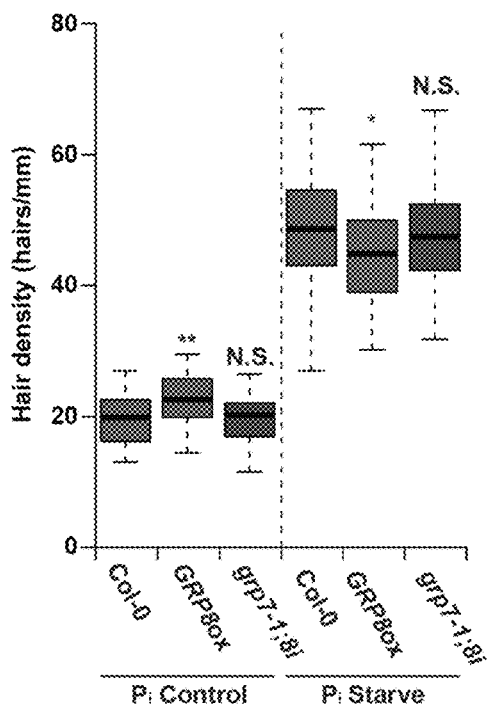

Acid phosphatases are secreted from the root epidermis, therefore phosphatase activity corresponds to root surface area (Gilbert et al., 1999; Tadano et al.). To determine whether increased phosphatase activity is a consequence of increased root hair cell number, we measured hair cell density under both normal and phosphate deprivation conditions. From this analysis we observed that GRP8ox plants exhibited significantly (p value<0.05; Wilcoxon test) decreased hair cell density under the starved conditions as compared to WT, while there was no change in grp7-1;8i plants (FIG. 6C), indicating that there is an uncoupling of GRP8-dependent regulation of cell fate decision from phosphate starvation response. Furthermore, these findings demonstrate that the increase in acid phosphatase activity is especially sizeable in GRP8ox plants (FIG. 6B), as there are fewer hair cells to secrete these enzymes during phosphate deprivation.

Figure 6D:
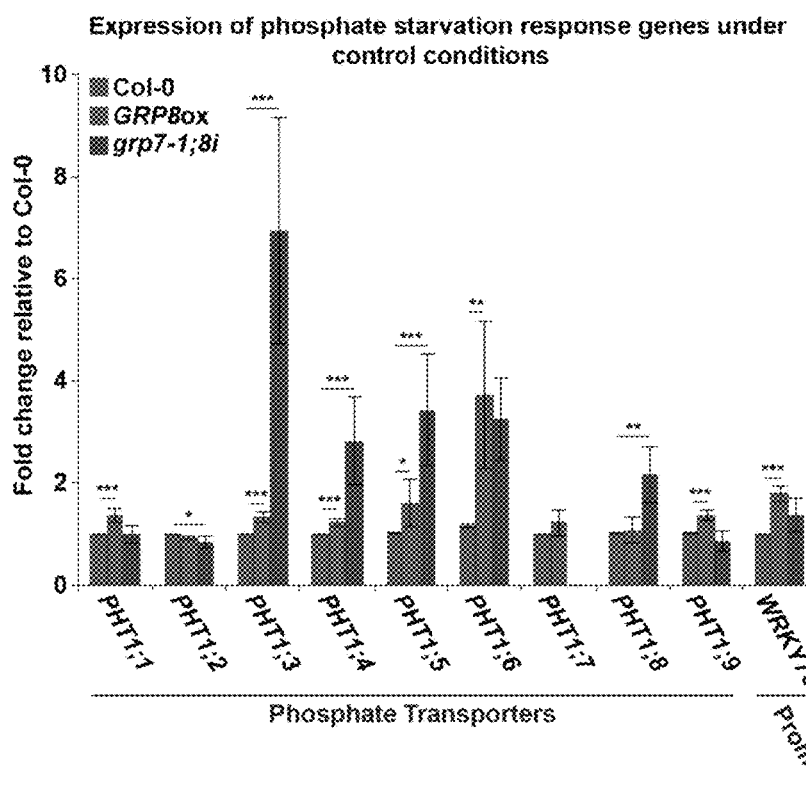

In order to better understand the roles of GRP8 and GRP7 in phosphate deprivation response, we measured the expression of numerous phosphate starvation response genes in the roots of GRP8ox and grp7-1;8i plants (Péret et al., 2011; Poirier and Bucher, 2002). To do this, we collected RNA from the roots of 8-day-old WT, GRP8ox, and grp7-1;8i seedlings under both control and phosphate starvation conditions and performed RT-qPCR on a panel of phosphate response genes. From this analysis, we observed a significant (all p values<0.05; Welch's t-test) increase in the levels of several PHOSPHATE TRANSPORTER 1 (PHT1) family genes in the roots of GRP8ox plants under normal growth conditions (FIG. 6D). Most of the PHT1 family genes are upregulated under phosphate starvation, providing a mechanism to maximize the uptake of phosphate when it is most scarce, allowing alleviation of the stress that the plant undergoes (Muchhal et al., 1996). Specifically, PHT1; 1 (AT5G43350) expression, which we found was increased in GRP8ox plants, has been linked to increased phosphate uptake and increased plant survival under phosphate starvation (Mitsukawa et al., 1997; Wang et al., 2014). In addition to heightened PHT1 levels, we found significantly (all p values<0.05; Welch's t-test) increased levels of the WRKY-domain containing transcription factor WRKY75 (AT5G13080) in GRP8ox as compared to WT roots (FIG. 6D). This is notable because WRKY75 is known to promote PHT1;1 transcription during phosphate starvation, and may be involved in the transcription of other PHT1 family genes (Chen et al., 2009; Devaiah et al., 2007; Wang et al., 2014). Interestingly, the grp7-1;8i plants exhibit upregulation of several PHT1 family genes (PHT1;3, PHT1;4, PHT1;5, PHT1;8) (FIG. 6D), indicating that there is a GRP7-dependent inhibition of several of these genes.

Therefore, these data indicate that there is a GRP8-dependent increase in the levels of most PHT1 family transcripts, while GRP7 also affects several of these mRNAs. We next aimed to determine if GRP8 directly binds to any of these phosphate deprivation response transcripts. As the α-GRP7/8 antibody binds to both GRP7 and GRP8 proteins, testing direct binding of GRP8 required performing RIP-qPCR in the roots of grp7-1 plants grown under phosphate deprivation. Using this assay, we tested for GRP8 binding to PHT1 family genes and WRKY75. Although there is no significant (all p values>0.05; Welch's t-test) enrichment of PHT1 family transcripts in GRP8 pulldown samples, we did observe a significant (all p values<0.05; Welch's t-test) enrichment of WRKY75 (FIG. 7A; p value<0.05; Welch's t-test) specifically in our α-GRP8 samples as compared to our IgG negative control. These data reveal that GRP8 binds to WRKY75 in vivo, leading to its altered transcript level. Thus, the GRP8-dependent regulation of WRKY75 results in increased PHT1 family phosphate transporter mRNA expression in the roots of 8-day-old seedlings.

As GRP8 promotes phosphate transporters, we next tested its role in alleviating both short-term and long-term phosphate starvation. We first measured phosphate levels in the aerial and root tissue of WT, GRP8ox, and grp7-1;8i seedlings after three days of phosphate starvation. This assay revealed significantly (p value<0.05; Welch's t-test) increased phosphate levels in both tissues in GRP8ox plants as compared to WT and grp7-1;8i seedlings (FIGS. 7B-7C). These results indicated that both phosphate uptake and phosphate efflux to the shoots are upregulated in plants with higher GRP8 levels. Additionally, we subjected plants to long-term (12-day) phosphate starvation and assayed both biomass and anthocyanin levels in the shoots of WT, GRP8ox, and grp7-1;8i seedlings, since phosphate starvation inhibits plant growth while promoting production of anthocyanin. We observed significantly (p value<0.05; Welch's t-test) greater biomass in the shoots of GRP8ox as compared to WT and grp7-1;8i plants (FIG. 7D). We also found significantly (p value<0.05; Welch's t-test) decreased anthocyanin accumulation in the aerial tissue of both GRP8ox and grp7-1;8i as compared to the WT plants (FIG. 7E). These data indicate that GRP8 is required for alleviating this plant stress by promoting increased phosphate uptake and biomass accumulation, while both GRP7 and GRP8 function in the reduction of the anthocyanin accumulation associated with phosphate starvation.

Discussion

Here, we use PIP-seq to examine both the RNA-protein interaction and RNA secondary structure landscapes of nuclei from root hair and non-hair cells, which comprise the Arabidopsis root epidermis. Analyzing highly pure populations of hair or non-hair cell nuclei revealed thousands of cell type specific protein-bound sites as well as many shared sites, which are enriched in the coding sequence of the mRNA transcriptomes of both cell types (FIG. 1). This study compares global patterns of RNA secondary structure and RNA-protein interactions across the nuclear transcriptomes of two distinct cell types. This large-scale analysis identifies distinct profiles in specific regions of mRNA transcripts. For instance, mRNAs found in both cell types exhibit an increase in protein binding in the CDS, which corresponds to a relative decrease in secondary structure (FIGS. 2A-2B). Interestingly, both RNA secondary structure and protein binding exhibit distinct patterns in the 3'UTR of root hair and nonhair cell nuclei (FIGS. 2C-2D). These profiles indicate that both RNA folding and protein binding can be regulated in a cell-type specific manner, providing two potential models to explain this phenomenon. First, cell type specific protein binding could regulate the folding of RNA transcripts, resulting in distinct folding patterns. Conversely, the distinct RNA folding patterns could in fact regulate protein binding. This latter model is supported by our findings that lncRNAs exhibit similar overall protein binding profiles while displaying distinct patterns of RNA secondary structure between root hair and non-hair cells (FIG. 2E-2F), suggesting that a different array of ssRNA- and dsRNA-binding RBPs are interacting with the distinctly structured lncRNAs found in these two cell types.

This study also reveals an interesting pattern in nuclear RNA folding. Specifically, our analysis reveals that in both root hair and non-hair cell nuclei the CDS is less structured than both UTRs (FIGS. 2A-2B), which is consistent with our nuclear PIP-seq performed in mixed nuclei from whole seedlings (Gosai et al., 2015). Although this pattern is consistent between all three nuclear PIP-seq datasets, the opposite pattern has been observed in studies performed on whole cell (mostly cytoplasmic) RNA populations. These whole cell studies have been performed on unopened flower buds utilizing ds/ssRNA-seq (Li et al., 2012a), as well as on whole seedlings with structure-seq (Ding et al., 2014). Although these studies were performed using different techniques in a variety of Arabidopsis tissues, these data support the idea that the nuclear and cytoplasmic transcriptomes may in fact have distinct RNA secondary structure profiles. As with cell type specific RNA folding, these distinct folding patterns could be due to different cohorts of RBPs in the nucleus and cytoplasm, and/or distinct post-transcriptional covalent modifications present in these cellular compartments.

However, these consistent results across various studies and structure probing techniques warrant additional analyses to better understand this phenomenon. In addition to describing global patterns, we used our PPS data to identify enriched protein-bound sequences and identify the RBPs that interact with a number of these sequences. More specifically, using RNA affinity chromatography we first identified SE as a candidate regulator of root hair cell development, while providing evidence of its preferred binding motif, a GGN repeat, in target RNAs (FIGS. 3A-3B). Phenotypic analyses reveal that SE inhibits root hair cell fate in a miRNA biogenesis-dependent manner (FIG. 3C), while terminating root hair tip growth in differentiated cells primarily by affecting the abundance of specific transcripts involved in this developmental process (FIGS. 3D and 4A-4E).

Through both RNA affinity chromatography and phenotypic analyses, we found that GRP8 promotes root hair cell fate in a GRP7-independent manner (FIGS. 5A-5). This finding is of particular interest since plants overexpressing GRP8 do not exhibit the deleterious aerial phenotypes described for se-1 (Clarke et al., 1999; Serrano-Cartagena et al., 1999), making this gene a candidate for engineering more stress resistant crop plants. This idea is further supported by our observations that GRP8 is upregulated upon phosphate starvation, and promotes increased acid phosphatase activity (FIGS. 6A-6D). Additionally, we found that GRP8 alone has substantial effects in promoting phosphate uptake, efflux, and biomass accumulation while simultaneously alleviating anthocyanin production during phosphate starvation (FIGS. 7A-7E). In fact, our findings provide support for a novel model of plant phosphate starvation response (FIG. 7F).

Figure 7A:
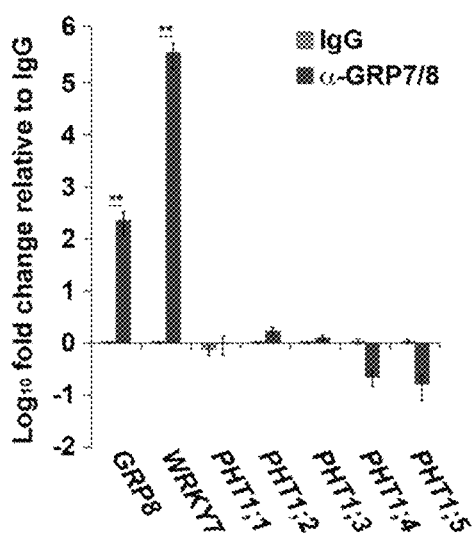
FIGS. 7A-7F: GRP8 alleviates phosphate deprivation stress (FIG. 7A) RIP-qPCR of root tissue from grp7-1 plants grown under phosphate starvation. RIP-qPCR was performed with a rabbit IgG (blue) or rabbit serum raised against GRP7 and GRP8 (green) graphed as fold change relative to α-IgG, n=4 (FIG. 7B-7C) Measurement of phosphate levels normalized to mass after 3-days of phosphate starvation in the shoots (FIG. 7B) or roots (FIG. 7C) of 8-day-old seedlings, n=12.
Figure 7B:
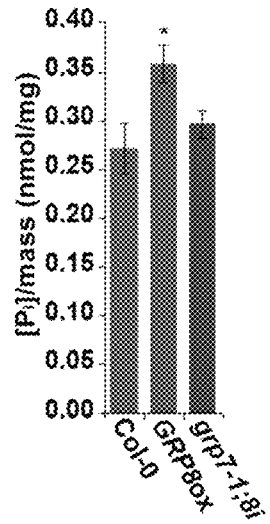
Figure 7C:
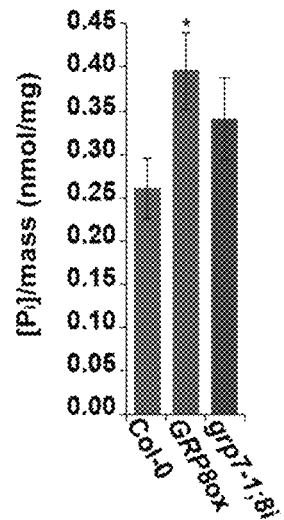
Figure 7D:
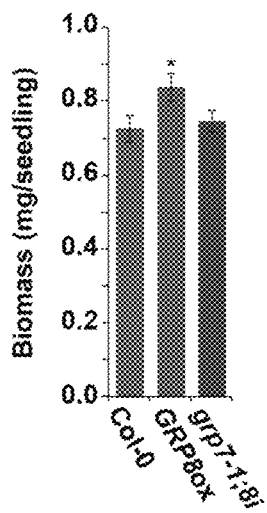
Figure 7E:
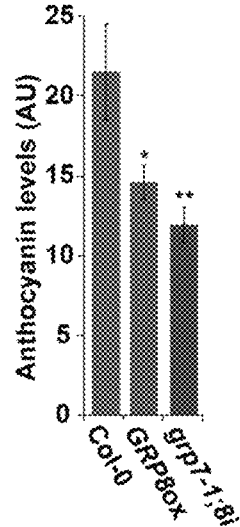
Figure 7F:
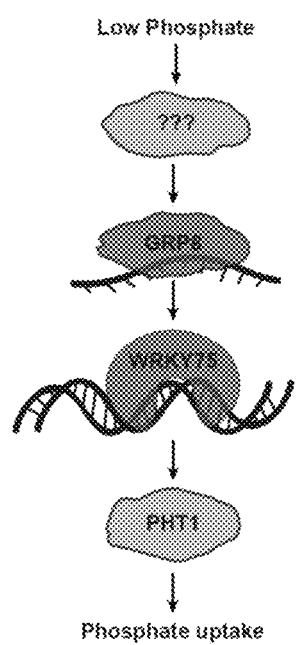

Specifically, we demonstrated that GRP8 is dramatically upregulated during phosphate starvation (FIG. 6A), and promotes the abundance of mRNAs encoding phosphate transporters and transcription factors that regulate their gene expression (FIG. 7B), while directly interacting with the transcript of one of these transcription factors (WRKY75) (FIG. 7A). The increase in PHT1 mRNA abundance likely explains the increased phosphate levels and biomass accumulation in GRP8 overexpressing plants (FIGS. 7C-7D), as well as decreased anthocyanin accumulation in the aerial tissues (FIG. 7E). Thus, present invention encompasses use of nucleic acids encoding GRP8 for over expressing this protein in order to generate stress resistant crop plants.

REFERENCES

Aichinger, E., Villar, C. B. R., Farrona, S., J. C., R., Hennig, L., and Kohler, C. (2009). CHD3 Proteins and Polycomb Group Proteins Antagonistically Determine Cell Identity in *Arabidopsis*. PLoS Genet. 5, e1000605.

Bailey, T. L., Boden, M., Buske, F. A., Frith, M., Grant, C. E., Clementi, L., Ren, J., Li, W. W., and Noble, W. S. (2009). MEME SUITE: tools for motif discovery and searching. Nucleic Acid Res. 37, W202-W208.

Bates, T. R., and Lynch, J. P. (1996). Stimulation of root hair elongation in *Arabidopsis thaliana* by low phosphorus availability. Plant Cell Environ. 19, 529-538.

Berkowitz, N. D., Silverman, I. M., Childress, D. M., Kazan, H., Wang, L.-S., and Gregory, B. D. (2016). A comprehensive database of high-throughput sequencing-based RNA secondary structure probing data (Structure Surfer). BMC Bioinformatics 17, 215.

Bernhardt, C., Lee, M. M., Gonzalez, A., Zhang, F., Lloyd, A., and Schiefelbein, J. (2003). The bHLH genes GLABRA3 (GL3) and ENHANCER OF GLABRA3 (EGL3) specify epidermal cell fate in the *Arabidopsis* root. Development 130.

Buratti, E., Muro, A. F., Giombi, M., Gherbassi, D., Iaconcig, A., and Baralle, F. E. (2001). RNA Folding Affects the Recruitment of SR Proteins by Mouse and Human Polypurinic Enhancer Elements in the Fibronectin EDA Exon. Mol Cell Biol 24, 1387-1400.

Chen, Y.-F., Li, L.-Q., Xu, Q., Kong, Y.-H., Wang, H., and Wu, W.-H. (2009). The WRKY6 transcription factor modulates PHOSPHATE1 expression in response to low Pi stress in *Arabidopsis*. Plant Cell 21, 3554-3566.

Clarke, J. H., Tack, D., Findlay, K., Van Montagu, M., and Van Lijsebettens, M. (1999). The SERRATE locus controls the formation of the early juvenile leaves and phase length in *Arabidopsis*. Plant J. Cell Mol. Biol. 20, 493-501.

Cooper, T. A., Wan, L., and Dreyfuss, G. (2009). RNA and disease. Cell 136, 777-793.

Cormack, R. G. H. (1935). The development of root hairs by *Elodea canadensis*. New Phytol 34, 19-25.

Cormack, R. G. H. (1949). The development of root hairs in angiosperms. Bot Rev 15, 583-612.

Cruz, J. A., and Westhof, E. (2009). The Dynamic Landscapes of RNA Architecture. Cell 136, 604-609.

Deal, R. B., and Henikoff, S. (2010). A Simple Method for Gene Expression and Chromatin Profiling of Individual Cell Types within a Tissue. Dev. Cell 18, 1030-1040.

Devaiah, B. N., Karthikeyan, A. S., and Raghothama, K. G. (2007). WRKY75 transcription factor is a modulator of phosphate acquisition and root development in *Arabidopsis*. Plant Physiol. 143, 1789-1801.

DiCristina, M. D., Sessa, G., Dolan, L., Linstead, P., Baima, S., Ruberti, I., and Morelli, G. (1996). The *Arabidopsis* Athb-10 (GLABRA2) is an HD-Zip protein required for regulation of root hair development. Plant J. 10, 393-402.

Ding, Y., Tang, Y., Kwok, C. K., Zhang, Y., Bevilacqua, P. C., and Assmann, S. M. (2014). In vivo genome-wide profiling of RNA secondary structure reveals novel regulatory features. Nature 505, 696-700.

Dolan, L., Janmaat, K., Willemsen, V., Linstead, P., Poethig, S., Roberts, K., and Scheres, B. (1993). Cellular organisation of the *Arabidopsis thaliana* root. Development 119, 71-84.

Dong, Z., Han, M.-H., and Fedoroff, N. (2008). The RNA-binding proteins HYL1 and SE promote accurate in vitro processing of pri-miRNA by DCL1. Proc. Natl. Acad. Sci. U.S.A 105, 9970-9975.

Furuta, K., Kubo, M., Sano, K., Demura, T., Fukuda, H., Liu, Y.-G., Shibata, D., and Kakimoto, T. (2011). The CKH2/PKL Chromatin Remodeling Factor Negatively Regulates Cytokinin Responses in *Arabidopsis* Calli. Pland Cell Physiol. 52, 618-628.

Gahoonia, T. S., Nielsen, N. E., Joshi, P. A., and Jahoor, A. A root hairless barley mutant for elucidating genetic of root hairs and phosphorus uptake. Plant Soil 235, 211-219.

Galway, M. E., Masucci, J. D., Lloyd, A. M., Walbot, V., Davis, R. W., and Schiefelbein, J. W. (1994). The TTG gene is required to specify epidermal cell fate and cell patterning in the *Arabidopsis* root. Dev. Biol. 166, 740-754.

Gilbert, G. A., Knight, J. D., Vance, C. P., and Allan, D. L. (1999). Acid phosphatase activity in phosphorus-deficient white lupin roots. Plant Cell Environ. 22, 801-810.

Glisovic, T., Bachorik, J. L., Yong, J., and Dreyfuss, G. (2008). RNA-binding proteins and post-transcriptional gene regulation. FEBS Lett. 582, 1977-1986.

Gosai, S. J., Foley, S. W., Wang, D., Silverman, I. M., Selamoglu, N., Nelson, A. D. L., Beilstein, M. A., Daldal, F., Deal, R. B., and Gregory, B. D. (2015). Global Analysis of the RNA-Protein Interaction and RNA Secondary Structure Landscapes of the *Arabidopsis* Nucleus. Mol Cell 57, 376-388.

Grierson, C., Nielsen, E., Ketelaarc, T., and Schiefelbein, J. (2014). Root Hairs. In The *Arabidopsis* Book, (The American Society of Plant Biologists), p. e0172.

Han, H., Irimia, M., Ross, P. J., Sung, H. K., Alipanahi, B., David, L., Golipour, A., Gabut, M., Michael, I. P., Nachman, E. N., et al. (2013). MBNL proteins repress ES-cell-specific alternative splicing and reprogramming. Nature 498, 241-245.

Heckrath, G., Brookes, P. C., Poulton, P. R., and Goulding, K. W. T. (1995). Phosphorus Leaching from Soils Containing Different Phosphorus Concentrations in the Broadbalk Experiment. J. Environ. Qual. 24, 904.

Hofer, R.-M. (1991). Root hairs. In Plant Roots The Hidden Half, Y. Waisel, A. Eshel, and U. Kafkafi, eds. pp. 129-148.

Jangi, M., and Sharp, P. A. (2014). Building robust transcriptomes with master splicing factors. Cell 159, 487-498.

Kaida, D., Berg, M. G., Younis, I., Kasim, M., Singh, L. N., Wan, L., and Dreyfuss, G. (2010). U1 snRNP protects pre-mRNAs from premature cleavage and polyadenylation. Nature 468, 664-668.

Kang, N. Y., Lee, H. W., and Kim, J. (2013). The AP2/EREBP Gene PUCHI Co-Acts with LBD16/ASL18 and LBD18/ASL20 Downstream of ARF7 and ARF19 to Regulate Lateral Root Development in *Arabidopsis*. Pland Cell Physiol. 54, 1326-1334.

Lan, P., Li, W., Lin, W.-D., Santi, S., and Schmidt, W. (2013). Mapping gene activity of *Arabidopsis* root hairs. Genome Biol. 14, R67.

Laubinger, S., Sachsenberg, T., Zeller, G., Busch, W., Lohmann, J. U., Rätsch, G., and Weigel, D. (2008). Dual roles of the nuclear cap-binding complex and SERRATE in pre-mRNA splicing and microRNA processing in *Arabidopsis thaliana*. Proc. Natl. Acad. Sci. U.S.A 105, 8795-8800.

Lebedeva, S., Jens, M., Theil, K., Schwanhausser, B., Selbach, M., Landthaler, M., and Rajewsky, N. (2011). Transcriptome-wide analysis of regulatory interactions of the RNA-binding protein HuR. Mol Cell 43, 340-352.

Lee, M. M., and Schiefelbein, J. (2002). Cell pattern in the *Arabidopsis* root epidermis determined by lateral inhibition with feedback. Plant Cell 14, 611-618.

Lewinski, M., Hallmann, A., and Staiger, D. (2016). Genome-wide identification and phylogenetic analysis of plant RNA binding proteins comprising both RNA recognition motifs and contiguous glycine residues. Mol. Genet. Genomics MGG 291, 763-773.

Lewis, B. P., Green, R. E., and Brenner, S. E. (2003). Evidence for the widespread coupling of alternative splicing and nonsense-mediated mRNA decay in humans. Proc Natl Acad Sci 100, 189-192.

Li, F., Zheng, Q., Vandivier, L. E., Willmann, M. R., Chen, Y., and Gregory, B. D. (2012a). Regulatory Impact of RNA Secondary Structure across the *Arabidopsis* Transcriptome. Plant Cell 24, 4346-4359.

Li, F., Zheng, Q., Ryvkin, P., Dragomir, I., Desai, Y., Aiyer, S., Valladares, O., Yang, J., Bambina, S., Sabin, L. R., et al. (2012b). Global Analysis of RNA Secondary Structure in Two Metazoans. Cell Rep. 1, 69-82.

Linkohr, B. I., Williamson, L. C., Fitter, A. H., and Leyser, H. M. O. (2002). Nitrate and phosphate availability and distribution have different effects on root system architecture of *Arabidopsis*. Plant J. 29, 751-760.

Liu, J., Jung, C., Xu, J., Wang, H., Deng, S., Bernad, L., Arenas-Huertero, C., and Chua, N. H. (2012). Genome-Wide Analysis Uncovers Regulation of Long Intergenic Noncoding RNAs in *Arabidopsis*. Plant Cell 24, 4333-4345.

Lobbes, D., Rallapalli, G., Schmidt, D. D., Martin, C., and Clarke, J. (2006). SERRATE: a new player on the plant microRNA scene. EMBO Rep. 7, 1052-1058.

Lynch, J. P., and Brown, K. M. Topsoil foraging—an architectural adaptation of plants to low phosphorus availability. Plant Soil 237, 225-237.

Lyons, E., and Freeling, M. (2008). How to usefully compare homologous plant genes and chromosomes as DNA sequences. Plant J. 53, 661-673.

Ma, Z., Bielenberg, D. G., Brown, K. M., and Lynch, J. P. (2001). Regulation of root hair density by phosphorus availability in *Arabidopsis thaliana*. Plant Cell Environ. 24, 459-467.

Masucci, J. D., and Schiefelbein, J. W. (1996). The rhd6 mutation of *Arabidopsis thaliana* alters root-hair initiation through an auxin- and ethylene-associated process. Plant Physiol. 106, 1335-1346.

Mei, H., Cheng, N. H., Zhao, J., Park, S., Escareno, R. A., Pittman, J. K., and Hirschi, K. D. (2009). Root development under metal stress in *Arabidopsis thaliana* requires the H+/cation antiporter CAX4. New Phytol. 183, 95-105.

Meisner, C. A., and Karnok, K. J. (1991). Root Hair Occurrence anld Variation with Environment. Agron. J. 83, 814.

Mitsukawa, N., Okumura, S., Shirano, Y., Sato, S., Kato, T., Harashima, S., and Shibata, D. (1997). Overexpression of an *Arabidopsis thaliana* high-affinity phosphate transporter gene in tobacco cultured cells enhances cell growth under phosphate-limited conditions. Proc. Natl. Acad. Sci. U.S.A 94, 7098-7102.

Muchhal, U. S., Pardo, J. M., and Raghothama, K. G. (1996). Phosphate transporters from the higher plant *Arabidopsis thaliana*. Proc. Natl. Acad. Sci. U.S.A 93, 10519-10523.

Muiño, J. M., Kaufmann, K., van Ham, R. C. H. J., Angenent, G. C., and Krajewski, P. (2011). ChIP-seq Analysis in R (CSAR): An R package for the statistical detection of protein-bound genomic regions. Plant Methods 7.

Niu, Y. F., Chai, R. S., Jin, G. L., Wang, H., Tang, C. X., and Zhang, Y. S. (2013). Responses of root architecture development to low phosphorus availability: a review. Ann. Bot. 112, 391-408.

OECD, and FAO (2012). OECD-FAO Agricultural Outlook 2012 (Paris: Organisation for Economic Co-operation and Development).

Ogas, J., Kaufmann, S., Henderson, J., and Somerville, C. (1999). PICKLE is a CHD3 chromatin-remodeling factor that regulates the transition from embryonic to vegetative development in *Arabidopsis*. PNAS 96, 13839-13844.

Olesen, J. E., and Bindi, M. (2002). Consequences of climate change for European agricultural productivity, land use and policy. Eur. J. Agron. 16, 239-262.

Patrick, W. H., and Khalid, R. A. (1974). Phosphate Release and Sorption by Soils and Sediments: Effect of Aerobic and Anaerobic Conditions. Science 186, 53-55.

Péret, B., Clément, M., Nussaume, L., and Desnos, T. (2011). Root developmental adaptation to phosphate starvation: better safe than sorry. Trends Plant Sci. 16, 442-450.

Poirier, Y., and Bucher, M. (2002). Phosphate transport and homeostasis in *Arabidopsis*. Arab. Book Am. Soc. Plant Biol. 1, e0024.

Raczynska, K. D., Stepien, A., Kierzkowski, D., Kalak, M., Bajczyk, M., McNicol, J., Simpson, C. G., Szweykowska-Kulinska, Z., Brown, J. W. S., and Jarmolowski, A. (2014). The SERRATE protein is involved in alternative splicing in *Arabidopsis thaliana*. Nucleic Acids Res. 42, 1224-1244.

Ray, D. K., Mueller, N. D., West, P. C., and Foley, J. A. (2013). Yield Trends Are Insufficient to Double Global Crop Production by 2050. PLOS ONE 8, e66428.

Reymond, M., Svistoonoff, S., Loudet, O., Nussaume, L., and Desnos, T. (2006). Identification of QTL controlling root growth response to phosphate starvation in *Arabidopsis thaliana*. Plant Cell Environ. 29, 115-125.

Rosenzweig, C., and Parry, M. L. (1994). Potential impact of climate change on world food supply. Nature 367, 133-138.

Ryu, K. H., Kang, Y. H., Park, Y., Hwang, I., Schiefelbein, J., and Lee, M. M. (2005). The WEREWOLF MYB protein directly regulates CAPRICE transcription during cell fate specification in the *Arabidopsis* root epidermis. Dev. Camb. Engl. 132, 4765-4775.

Schöning, J. C., Streitner, C., Meyer, I. M., Gao, Y., and Staiger, D. (2008). Reciprocal regulation of glycine-rich RNA-binding proteins via an interlocked feedback loop coupling alternative splicing to nonsense-mediated decay in *Arabidopsis*. Nucleic Acids Res. 36, 6977-6987.

Serrano-Cartagena, J., Robles, P., Ponce, M. R., and Micol, J. L. (1999). Genetic analysis of leaf form mutants from the *Arabidopsis* Information Service collection. Mol. Gen. Genet. MGG 261, 725-739.

Sharp, P. A. (2009). The centrality of RNA. Cell 136, 577-580.

Silverman, I. M., Li, F., Alexander, A., Goff, L., Trapnell, C., Rinn, J. L., and Gregory, B. D. (2014). RNase-mediated protein footprint sequencing reveals protein-binding sites throughout the human transcriptome. Genome Biol. 15, R3.

Song, S.-K., Ryu, K. H., Kang, Y. H., Song, J. H., Cho, Y.-H., Yoo, S.-D., Schiefelbein, J., and Lee, M. M. (2011). Cell fate in the *Arabidopsis* root epidermis is determined by competition between WEREWOLF and CAPRICE. Plant Physiol. 157, 1196-1208.

Streitner, C., Köster, T., Simpson, C. G., Shaw, P., Danisman, S., Brown, J. W. S., and Staiger, D. (2012). An hnRNP-like RNA-binding protein affects alternative splicing by in vivo interaction with transcripts in *Arabidopsis thaliana*. Nucleic Acids Res. 40, 11240-11255.

Tadano, T., Ozawa, K., Sakai, H., Osaki, M., and Matsui, H. Secretion of acid phosphatase by the roots of crop plants under phosphorus-deficient conditions and some properties of the enzyme secreted by lupin roots. Plant Soil 155-156, 95-98.

Tilman, D., Balzer, C., Hill, J., and Befort, B. L. (2011). Global food demand and the sustainable intensification of agriculture. Proc. Natl. Acad. Sci. U.S.A 108, 20260-20264.

Tominaga, R., Iwata, M., Okada, K., and Wada, T. (2007). Functional analysis of the epidermal-specific MYB genes CAPRICE and WEREWOLF in *Arabidopsis*. Plant Cell 19, 2264-2277.

Ule, J., Jensen, K. B., Ruggiu, M., Mele, A., Ule, A., and Darnell, R. B. (2003). CLIP Identifies Nova-Regulated RNA Networks in the Brain. Science 302, 1212-1215.

Vandivier, L. E., Campos, R., Kuksa, P. P., Silverman, I. M., Wang, L.-S., and Gregory, B. D. (2015). Chemical Modifications Mark Alternatively Spliced and Uncapped Messenger RNAs in *Arabidopsis*. Plant Cell 27, 3024-3037.

Vandivier, L. E., Anderson, S. J., Foley, S. W., and Gregory, B. D. (2016). The Conservation and Function of RNA Secondary Structure in Plants. Annu. Rev. Plant Biol. 67, 463-488.

Venables, J. P., Lapasset, L., Gadea, G., Fort, P., Klinck, R., Irimia, M., Vignal, E., Thibault, P., Prinos, P., Chabot, B., et al. (2013). MBNL1 and RBFOX2 coop-erate to establish a splicing programme involved in pluripotent stem cell differ-entiation. Nat. Commun. 4.

Wada, T., Tachibana, T., Shimura, Y., and Okada, K. (1997). Epidermal cell differentiation in *Arabidopsis* determined by a Myb homolog, CPC. Science 277, 1113-1116.

Wang, D., and Deal, R. B. (2015). Epigenome profiling of specific plant cell types using a streamlined INTACT protocol and ChIP-seq. Methods Mol. Biol. Clifton N. J. 1284, 3-25.

Wang, H., Xu, Q., Kong, Y.-H., Chen, Y., Duan, J.-Y., Wu, W.-H., and Chen, Y.-F. (2014). *Arabidopsis* WRKY45 transcription factor activates PHOSPHATE TRANSPORTER1;1 expression in response to phosphate starvation. Plant Physiol. 164, 2020-2029.

Warzecha, C. C., Sato, T. K., Nabet, B., Hogenesch, J. B., and Carstens, R. P. (2009). ESRP1 and ESRP2 are epithelial cell-type-specific regulators of FGFR2 splicing. Mol. Cell 33, 591-601.

Whittington, A. T., Vugrek, O., Wei, K. J., Hasenbein, N. G., Sugimoto, K., Rashbrooke, M. C., and Wasteneys, G. O. (2001). MOR1 is essential for organizing cortical microtubules in plants. Nature 411, 610-613.

Williamson, L. C., Ribrioux, S. P. C. P., Fitter, A. H., and Leyser, H. M. O. (2001). Phosphate Availability Regulates Root System Architecture in *Arabidopsis*. Plant Physiol. 126, 875-882.

Woo, J., MacPherson, C. R., Liu, J., Wang, H., Kiba, T., Hannah, M. A., Wang, X.-J., Bajic, V. B., and Chua, N.-H. (2012). The response and recovery of the *Arabidopsis thaliana* transcriptome to phosphate starvation. BMC Plant Biol. 12, 62.

Yang, L., Liu, Z., Lu, F., Dong, A., and Huang, H. (2006). SERRATE is a novel nuclear regulator in primary microRNA processing in *Arabidopsis*. Plant J. Cell Mol. Biol. 47, 841-850.

Younis, I., Dittmar, K., Wang, W., Foley, S. W., Berg, M. G., Hu, K. Y., Wei, Z., Wan, L., and Dreyfuss, G. (2013). Minor introns are embedded molecular switches regulated by highly unstable U6atac snRNA. eLife 2, e00780.

What is claimed is:

1. A method for producing a plant exhibiting increased root hair formation and increased resistance to phosphate starvation comprising,
    a) introducing a nucleic acid construct encoding glycine rich protein 8 (GRP8) of SEQ ID NO: 4 into a plant cell, said construct causing over expression of GRP8 in said plant cell,
    b) generating a GRP8 overexpressing plant from said plant cell,
    c) measuring root hair cell density and, or, root hair cell acid phosphatase activity in the plant of step b) said plant exhibiting increasing root hair formation and resistance to phosphate starvation when compared to plants lacking said nucleic acid construct.

2. The method of claim 1, wherein the nucleic acid encoding GRP8 is under the control of a constitutive promoter.

3. The method of claim 1, wherein the nucleic acid encoding GRP 8 expression is under the control of an inducible promoter.

4. The method of claim 1, wherein GRP 8 expression is under the control of a tissue specific promoter.

5. The method of claim 1, wherein said plant is selected from barley, tomato, *Brassica rapa, Camelina sativa, Zea mays*, rice, soybean and sunflower.

* * * * *

SEQUENCE LISTING

```
<160> NUMBER OF SEQ ID NOS: 4

<210> SEQ ID NO 1
<211> LENGTH: 510
<212> TYPE: DNA
<213> ORGANISM: Arabidopsis thaliana

<400> SEQUENCE: 1
atgtctgaag ttgagtaccg gtgctttgtc ggcggccttg cctgggccac caatgatgaa      60
gatcttcaaa ggacgttctc acagttcggc gacgttatcg attctaagat cattaacgac     120
cgcgagagtg gaagatcaag gggattcgga ttcgtcacct tcaaggacga gaaagccatg     180
agggatgcga ttgaagagat gaacggtaaa gagctcgatg gacgtgtcat caccgtgaac     240
gaggctcagt cgagaggtag cggcggtggc ggaggaggcc gtggtggaag cggtggtggt     300
taccgcagcg gaggcggtgg tggatactca ggaggcggtg gcggcggata ctcaggagga     360
ggcggtggtg gttacgagag acgtagcgga ggttacggat ctggtggagg cggtggtggc     420
cgaggatacg gtggtggtgg acgccgtgag ggaggtggct acggaggcgg tgatggtgga     480
agttacggag gcggtggtgg cggctggtaa                                       510
```

```
<210> SEQ ID NO 2
<211> LENGTH: 1181
<212> TYPE: DNA
<213> ORGANISM: Arabidopsis thaliana

<400> SEQUENCE: 2
aaccctagtt attacgtcac acctgttcta taaattaagg ctgcgtctta tcacctcaaa      60
tcacataagt ctctctctta cattttgaaa ccctaatttc tcttcttttc cccaaaaaaa     120
aatgtctgaa gttgagtacc ggtgctttgt cggcggcctt gcctgggcca ccaatgatga     180
agatcttcaa aggacgttct cacagttcgg cgacgttatc gattctaagg tctgttacac     240
gagagatcgg tctcccggat cgagccgatt ccgatgattc tgatcctcga cggatctgat     300
tccgatctgt ttctctgtta cttgattcga ttactgttac tatgttctct ctcgttcttt     360
gttactgtta cttaatttgt cccatcggta cgttcatctt cctgcttcta tgagctcgga     420
gatcgatcga tttttgcttt atattcatcg ctttgtttta tattccttcc acgattgttt     480
ttgctgatgt gtatgatttt gtttgtttac agatcattaa cgaccgcgag agtggaagat     540 caagggggatt cggattcgtc accttcaagg acgagaaagc catgagggat gcgattgaag     600
agatgaacgg taaagagctc gatggacgtg tcatcaccgt gaacgaggct cagtcgagag     660
gtagcggcgg tggcggagga ggccgtggtg aagcggtgg tggttaccgc agcggaggcg       720
gtggtggata tcaggaggc ggtggcggcg gatactcagg aggaggcggt ggtggttacg       780
agagacgtag cggaggttac ggatctggtg gaggcggtgg tggccgagga tacggtggtg     840
gtggacgccg tgagggaggt ggctacggag gcggtgatgg tggaagttac ggaggcggtg     900
gtggcggctg gtaatcaaag atagagttgt ttgcgtgctg ctgctctgtt tttggtttag     960
atttggtttt gtgtcaccac ttctggtttg gttatcgttc gtttggttta cttttttgat    1020
gaaacagttt cgtttaagtc ttctttgtct ggaacgaaat gttaattcgc gtgttgttta    1080
ctaaatttat aacgtttcct tttaaccaga ttcgagattt cccctcaaat aatttatctt    1140
gttagacaca tgtatttaat cgaacagcag ctaaaggatt c                         1181

<210> SEQ ID NO 3
<211> LENGTH: 898
<212> TYPE: DNA
<213> ORGANISM: Arabidopsis thaliana

<400> SEQUENCE: 3
aaccctagtt attacgtcac acctgttcta taaattaagg ctgcgtctta tcacctcaaa      60
tcacataagt ctctctctta cattttgaaa ccctaatttc tcttcttttc cccaaaaaaa     120
aatgtctgaa gttgagtacc ggtgctttgt cggcggcctt gcctgggcca ccaatgatga     180
agatcttcaa aggacgttct cacagttcgg cgacgttatc gattctaaga tcattaacga     240
ccgcgagagt ggaagatcaa ggggattcgg attcgtcacc ttcaaggacg agaaagccat     300
gagggatgcg attgaagaga tgaacggtaa agagctcgat ggacgtgtca tcaccgtgaa     360
cgaggctcag tcgagaggta gcggcggtgg cggaggaggc cgtggtggaa gcggtggtgg     420
ttaccgcagc ggaggcggtg gtggatactc aggaggcggt ggcggcggat actcaggagg     480
aggcggtggt ggttacgaga gacgtagcgg aggttacgga tctggtggag gcggtggtgg     540
ccgaggatac ggtggtggtg gacgccgtga gggaggtggc tacggaggcg gtgatggtgg     600
aagttacgga ggcggtggtg gcggctggta atcaaagata gagttgtttg cgtgctgctg     660
ctctgttttt ggtttagatt tggttttgtg tcaccacttc tggtttggtt atcgttcgtt     720
```

```
tggtttactt ttttgatgaa acagtttcgt ttaagtcttc tttgtctgga acgaaatgtt    780
aattcgcgtg ttgtttacta aatttataac gtttcctttt aaccagattc gagattttcc    840
ctcaaataat ttatcttgtt agacacatgt atttaatcga acagcagcta aaggattc      898
```

<210> SEQ ID NO 4
<211> LENGTH: 169
<212> TYPE: PRT
<213> ORGANISM: Arabidopsis thaliana

<400> SEQUENCE: 4

```
Met Ser Glu Val Glu Tyr Arg Cys Phe Val Gly Gly Leu Ala Trp Ala
1               5                   10                  15

Thr Asn Asp Glu Asp Leu Gln Arg Thr Phe Ser Gln Phe Gly Asp Val
            20                  25                  30

Ile Asp Ser Lys Ile Ile Asn Asp Arg Glu Ser Gly Arg Ser Arg Gly
        35                  40                  45

Phe Gly Phe Val Thr Phe Lys Asp Glu Lys Ala Met Arg Asp Ala Ile
    50                  55                  60

Glu Glu Met Asn Gly Lys Glu Leu Asp Gly Arg Val Ile Thr Val Asn
65                  70                  75                  80

Glu Ala Gln Ser Arg Gly Ser Gly Gly Gly Gly Gly Arg Gly Gly
                85                  90                  95

Ser Gly Gly Gly Tyr Arg Ser Gly Gly Gly Gly Tyr Ser Gly Gly
                100                 105                 110

Gly Gly Gly Gly Tyr Ser Gly Gly Gly Gly Gly Tyr Glu Arg Arg
                115                 120                 125

Ser Gly Gly Tyr Gly Ser Gly Gly Gly Gly Gly Arg Gly Tyr Gly
    130                 135                 140

Gly Gly Gly Arg Arg Glu Gly Gly Tyr Gly Gly Gly Asp Gly Gly
145                 150                 155                 160

Ser Tyr Gly Gly Gly Gly Gly Trp
                165
```